(12) United States Patent
Karimzadeh et al.

(10) Patent No.: US 7,661,146 B2
(45) Date of Patent: Feb. 9, 2010

(54) METHOD AND SYSTEM FOR PROVIDING A SECURE MULTI-USER PORTABLE DATABASE

(75) Inventors: Mansour Aaron Karimzadeh, Great Neck, NY (US); Mark Douglas Schaeffer, San Ramon, CA (US); F. Avraham Dilmanian, Yaphank, NY (US); Farshad Namdar, Forest Hills, NY (US)

(73) Assignee: PrivaMed, Inc., Carle Place, NY (US)

( * ) Notice: Subject to any disclaimer, the term of this patent is extended or adjusted under 35 U.S.C. 154(b) by 491 days.

(21) Appl. No.: 11/173,133

(22) Filed: Jul. 1, 2005

(65) Prior Publication Data

US 2007/0006322 A1    Jan. 4, 2007

(51) Int. Cl.
G06F 7/04 (2006.01)
G06F 17/30 (2006.01)
H04N 7/16 (2006.01)

(52) U.S. Cl. .......................... 726/27; 713/166
(58) Field of Classification Search .......... 705/2, 705/52, 75; 713/193, 156, 165, 166, 167, 713/173, 175; 726/9, 27, 28, 29, 30
See application file for complete search history.

(56) References Cited

U.S. PATENT DOCUMENTS

| | | | |
|---|---|---|---|
| 5,291,399 A * | 3/1994 | Chaco | 705/3 |
| 5,495,533 A * | 2/1996 | Linehan et al. | 713/155 |
| 5,899,998 A * | 5/1999 | McGauley et al. | 707/104.1 |
| 6,131,090 A * | 10/2000 | Basso et al. | 705/2 |
| 6,148,342 A * | 11/2000 | Ho | 709/225 |
| 6,212,635 B1 * | 4/2001 | Reardon | 713/165 |
| 6,272,470 B1 * | 8/2001 | Teshima | 705/3 |
| 6,289,450 B1 * | 9/2001 | Pensak et al. | 713/167 |
| 6,339,825 B2 * | 1/2002 | Pensak et al. | 713/158 |
| 6,449,721 B1 * | 9/2002 | Pensak et al. | 713/171 |
| 6,460,036 B1 * | 10/2002 | Herz | 707/10 |
| 6,463,417 B1 | 10/2002 | Schoenberg | |
| 6,466,671 B1 * | 10/2002 | Maillard et al. | 380/227 |
| 6,523,009 B1 * | 2/2003 | Wilkins | 705/2 |

(Continued)

OTHER PUBLICATIONS

Pierre Paradinas, Jean-jacques V, A Personal and Portable Database Server: the CQL Card, 1994, In Application of Databases, vol. 819 of LNCS, Vadstena.*

(Continued)

Primary Examiner—David García Cervetti
(74) Attorney, Agent, or Firm—Hoffmann & Baron, LLP

(57) ABSTRACT

A system and method for providing, managing, and accessing a multi-user secure portable database using secure memory cards is provided. The database has a secure portion for storing security keys and a non-secure portion for encrypted data files. Access to the encrypted data files is controlled by assigning access rights through an access control matrix to each encrypted data file according to a hierarchical structure of users. A user requesting access is identified in the hierarchy, associated with a key for allowing the requested access, and the requested access allowed to a file in accordance with the rights allocated through the access control matrix. A patient can selectively grant access to encrypted medical records on his card to a physician. Authentication of the owner/patient is preferably required. Other records required by emergency medical personnel are readable from the same card without requiring permission from the patient.

50 Claims, 16 Drawing Sheets

U.S. PATENT DOCUMENTS

| | | | |
|---|---|---|---|
| 6,602,298 B1* | 8/2003 | Kirshenbaum | 715/234 |
| 6,678,826 B1* | 1/2004 | Kelly et al. | 726/2 |
| 6,725,200 B1* | 4/2004 | Rost | 705/2 |
| 6,745,247 B1* | 6/2004 | Kawan et al. | 709/245 |
| 6,751,651 B2* | 6/2004 | Crockett | 709/203 |
| 6,772,952 B1* | 8/2004 | Macaire | 235/492 |
| 6,845,908 B2* | 1/2005 | Morita et al. | 235/382 |
| 6,862,614 B2* | 3/2005 | Paradinas et al. | 709/220 |
| 6,920,567 B1* | 7/2005 | Doherty et al. | 726/22 |
| 6,947,556 B1* | 9/2005 | Matyas et al. | 380/29 |
| 6,978,376 B2* | 12/2005 | Giroux et al. | 713/189 |
| 7,003,670 B2* | 2/2006 | Heaven et al. | 713/186 |
| 7,140,044 B2* | 11/2006 | Redlich et al. | 726/27 |
| 7,143,175 B2* | 11/2006 | Adams et al. | 709/229 |
| 7,146,644 B2* | 12/2006 | Redlich et al. | 726/27 |
| 7,155,739 B2* | 12/2006 | Bari et al. | 726/6 |
| 7,168,092 B2* | 1/2007 | King et al. | 726/9 |
| 7,171,411 B1* | 1/2007 | Lewis et al. | 707/9 |
| 7,266,702 B2* | 9/2007 | Hotti | 713/186 |
| 7,322,047 B2* | 1/2008 | Redlich et al. | 726/27 |
| 7,331,058 B1* | 2/2008 | Gladney | 726/2 |
| 7,356,460 B1* | 4/2008 | Kennedy et al. | 704/9 |
| 7,370,349 B2* | 5/2008 | Holvey et al. | 726/5 |
| 7,430,664 B2* | 9/2008 | Zhu et al. | 713/168 |
| 7,440,962 B1* | 10/2008 | Wong et al. | 707/102 |
| 7,452,278 B2* | 11/2008 | Chen et al. | 463/42 |
| 7,458,102 B2* | 11/2008 | Rogers et al. | 726/30 |
| 7,546,334 B2* | 6/2009 | Redlich et al. | 709/201 |
| 7,552,482 B2* | 6/2009 | Redlich et al. | 726/27 |
| 7,587,504 B2* | 9/2009 | Adams et al. | 709/229 |
| 2001/0052074 A1* | 12/2001 | Pensak et al. | 713/167 |
| 2002/0010679 A1* | 1/2002 | Felsher | 705/51 |
| 2002/0029340 A1* | 3/2002 | Pensak et al. | 713/182 |
| 2002/0077861 A1* | 6/2002 | Hogan | 705/2 |
| 2002/0078361 A1* | 6/2002 | Giroux et al. | 713/183 |
| 2002/0116478 A1* | 8/2002 | Paradinas et al. | 709/220 |
| 2002/0188854 A1* | 12/2002 | Heaven et al. | 713/186 |
| 2003/0033534 A1* | 2/2003 | Rand et al. | 713/185 |
| 2003/0055824 A1* | 3/2003 | Califano | 707/9 |
| 2003/0065626 A1* | 4/2003 | Allen | 705/76 |
| 2003/0093298 A1* | 5/2003 | Hernandez et al. | 705/2 |
| 2003/0130867 A1* | 7/2003 | Coelho et al. | 705/2 |
| 2003/0220876 A1* | 11/2003 | Burger et al. | 705/50 |
| 2004/0015723 A1* | 1/2004 | Pham et al. | 713/201 |
| 2004/0083123 A1 | 4/2004 | Kim et al. | |
| 2004/0086124 A1* | 5/2004 | Sasaki | 380/277 |
| 2004/0103000 A1 | 5/2004 | Owurowa et al. | |
| 2004/0111622 A1 | 6/2004 | Schoenberg | |
| 2004/0125402 A1* | 7/2004 | Kanai et al. | 358/1.15 |
| 2004/0238645 A1* | 12/2004 | Abellan Sevilla et al. | 235/492 |
| 2004/0243520 A1* | 12/2004 | Bishop et al. | 705/75 |
| 2005/0050367 A1* | 3/2005 | Burger et al. | 713/202 |
| 2005/0060586 A1* | 3/2005 | Burger et al. | 713/201 |
| 2005/0108096 A1* | 5/2005 | Burger et al. | 705/14 |
| 2005/0108201 A1* | 5/2005 | Abellan Sevilla et al. | 707/3 |
| 2005/0108295 A1* | 5/2005 | Karimisetty et al. | 707/200 |
| 2005/0116026 A1* | 6/2005 | Burger et al. | 235/380 |
| 2005/0197859 A1* | 9/2005 | Wilson et al. | 705/2 |
| 2005/0216755 A1* | 9/2005 | Lipsky et al. | 713/193 |
| 2006/0025696 A1* | 2/2006 | Kurzweil et al. | 600/509 |
| 2006/0041751 A1* | 2/2006 | Rogers et al. | 713/171 |
| 2007/0005396 A1* | 1/2007 | Lee | 705/3 |
| 2007/0055538 A1* | 3/2007 | Burton | 705/2 |
| 2007/0078677 A1* | 4/2007 | Hofstetter | 705/2 |

OTHER PUBLICATIONS

Luc Bouganim, Philippe Pucheral, Chip-Secured Data Access: Confidential Data on Untrusted Servers, 2002, VLDB Conference.*
Anciaux, et al., "PicoDBMS: Validation and Experience," *Proceedings of the 27th Very Large Database Conference*, Rome, Italy (2001).
Jean, et al., "Using Some Database Principles to Improve Cooperation in Multi-Application Smart Cards," 21st International Conference of the Chilean Computer Science Society (SCCC 2001), Nov. 6-8, 2001, Punta Arenas, Chile, IEEE Computer Society (2001).
Smart Card Management System Presentation by CIBC (Nov. 1998).
PrivaMed Patient Card Demonstration, PrivaMed, Inc. (2003).
Smart Card Alliance White Paper "HIPAA Compliance and Smart Cards: Solutions to Privacy and Security Requirements," Smart Card Alliance (Sep. 2003).
Patient Medical Information brochure.

* cited by examiner

FIG. 2

| | Create | Read | Update | Delete | User id |
|---|---|---|---|---|---|
| World | | | | | N/A |
| Group | | | | | Group name(s) |
| Individual | | | | | Individual name(s) |
| | | | | | |

FIG. 3

| | Create | Read | Update | Delete | User id |
|---|---|---|---|---|---|
| World | R | A | R | R | N/A |
| Group | R | (A) | A | R | Group name(s) |
| Individual (Entity) | A | (A) | (A) | A | Individual name(s) |
| | | | | | |

FIG. 4

| | Create | Read | Update | Delete |
|---|---|---|---|---|
| World | Restricted | | Restricted | Restricted |
| Group | Restricted | | Restricted | Restricted |
| Individual | | | | |

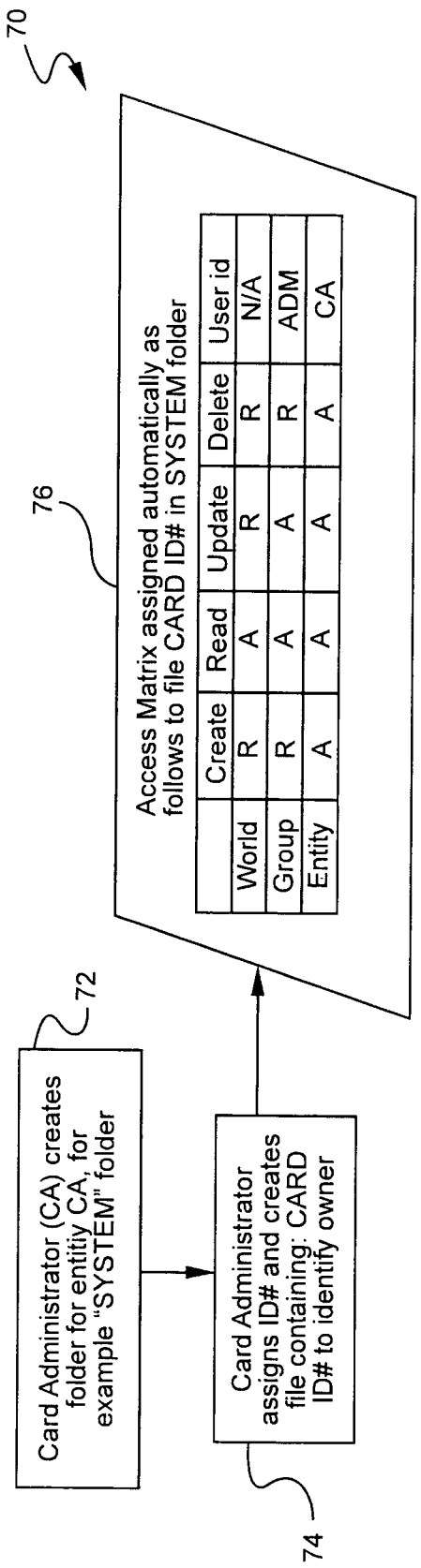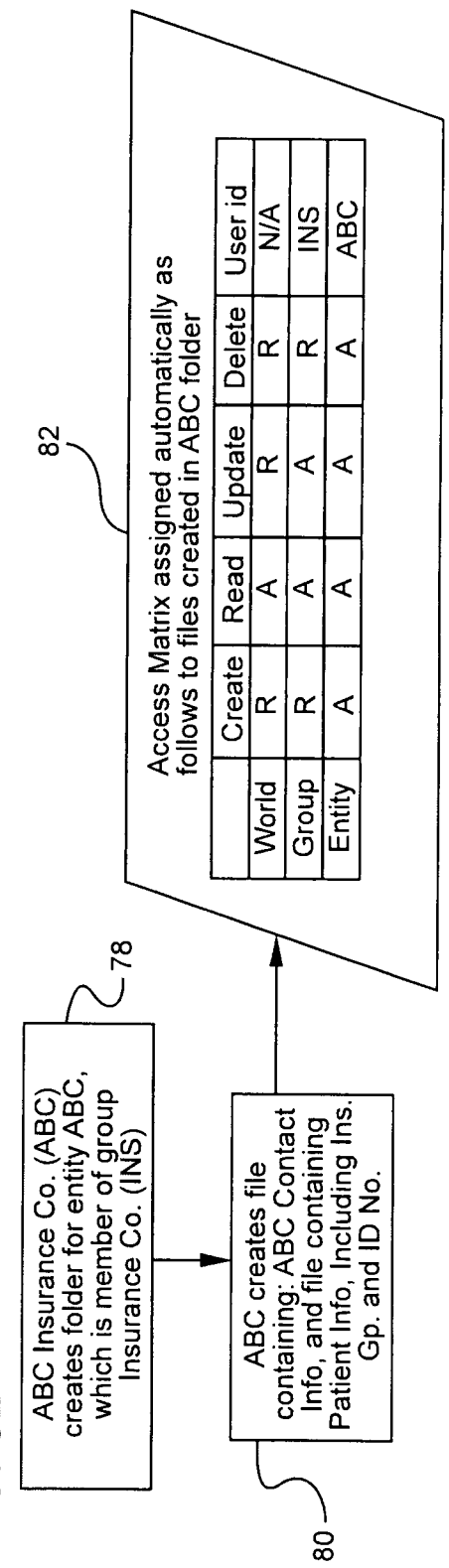

FIG. 7C

| Owner | Data | | Access | | | | Comments |
|---|---|---|---|---|---|---|---|
| | | | Create | Read | Update | Delete | |
| Insurance | | | Owner | World | Owner | Owner | |
| | Insurance company name | | | | | | |
| | Insurance ID | | | | | | |
| | Standard option list | | | | | | |
| | Standard option list | | | | | | |
| | Picture of patient | | | | | | |
| Patient | | | | | | | |
| | Name | | Owner | World | Owner | Owner | |
| | Address | | Owner | World | Owner | Owner | |
| | SSN | | Owner | World | Owner | Owner | |
| | Age, wieght, etc. | | Owner | World | Owner | Owner | |
| | Picture | | Owner | World | Owner | Owner | |
| | Standard preferences | | Owner | World | Owner | Owner | |
| | Critical Drug allergies/ medical conditions | | Owner/O | World Doctor/O | Doctor/O | Doctor/O | |
| | Medical history | | Doctor/O | EMT, Doctor/O | | | Copied from other records |
| | Summaries of Medical Conditions | | Doctor/O | EMT, Doctor/O | | | |
| Doctor | | | | | | | |
| | Appointments | | Owner | World | Owner | World | |
| | Visit medical notes | | Owner | Patient | Owner | None | |
| | Test results | | Owner | Patient | Owner | None | |
| | Prescription | | Owner | Owner, Patient | Pharmacy | Pharmacy | |
| | Billing record | | Owner | Patient | Owner | | |
| EMT | | | | | | | |
| | Log | | Owner | Patient | | | |
| Hospital | | | | | | | |
| | Info on stay (dates, room, resouces, etc.) | | Owner | Patient | | | |
| | Charts / medical information / results | | Owner | Patient | | | |
| | Billing record | | Owner | Patient | Owner | | |

A. Authenticate Dr. Against Patient card data

B. Authenticate Patient Against PIN / Biometrics

METHOD AND SYSTEM FOR PROVIDING A SECURE MULTI-USER PORTABLE DATABASE

The present invention relates generally to a system and method for providing a secure, portable database and, more particularly, to a system and method for providing the secure storage of and hierarchical multi-user access to privatized data on a portable database.

BACKGROUND

Conventionally, portable storage of data has been commercially available for electronically strong text, such as addresses and phone numbers, or for simple storage and access of a common type of digital media, such as music. These databases, commonly provided on flash memory cards or Universal Serial Bus (USB) tokens have nominal or no built-in security, since the intended use is for non-sensitive data storage and access for a single user. In other words, these products do not provide for the portable storage of secure, privatized data, and a means for multiple parties to access such protected data in a controlled way. There is a need for a portable, multi-user, secure database and a system and method for storage and retrieval of select data by an authorized user, which is not provided for in the prior art.

In particular, there is a need in the current fragmented health care system in the United States and in other countries for a generic database and network for the exchange of patient health information among different health-care providers. The U.S. health care system is made up of many entities spread over a large geographic area, with minimal or no communications or coordination among them for exchange of patient health data. Information is generally owned and kept by the health care provider generating the data, and will only be copied to another if expressly asked for. As a result, physicians do not have easy routine access to the patient's general medical records except for what they themselves produce. In addition, patients going from one health care provider to another usually do not have the relevant records and test results with them. This system results in a number of major problems including delays in diagnosis and treatment, inefficient use of time and resources, unnecessary repetition of tests, and errors in medical practices that could lead to thousands of deaths each year.

Finally, the physician's lack of immediate access to patient information also encourages fraud and abuse of our current health care system. The consequences of such abuse are increased insurance premiums, and, therefore, increased cost to the consumer. There is clearly a need, therefore, for a more accessible, portable, and efficient system for exchanging patient health information among different health-care providers.

There is also a need for a system and method of managing and accessing medical data that maintains a patient's privacy. In fact, as a result of the Health Insurance Portability and Accountability Act (HIPAA) enacted by Congress in 1996, U.S. health care providers are now mandated to maintain patient data in a private and secure manner. In accordance with HIPAA, patient health care information can only be divulged by a physician to other health care providers upon the consent of the patient.

Though some attempts have been made to implement an accessible electronic medical information system, none of them provide the accessibility, security, and portability needed to address the current problems in our health care system. U.S. Pat. No. 5,899,998 to McGauley et al., for example, discloses a method and system for maintaining and updating computerized medical records. The system includes a set of databases that propagate data from one database to the other over a network. Encryption techniques are used to maintain the security of the data only when it is being transmitted to other computers.

Similarly, U.S. Pat. No. 6,463,417 to Schoenberg discloses a method and system to allow access to patient data over a communications network. All patient medical records are stored on a number of computers. Access to these computers is only available via a communications network. Should the network fail, the access to the data will be lost. In addition, access to such a host-based database requires access to another provider's system or another insurance company's database, which may not be easily accessible due to business reasons.

U.S. Pat. No. 6,523,116 to Berman discloses a personal card that contains a public key to access a centralized database. The public key identifies the patient, whose medical record is needed, and allows access to the data. The card only provides the user access to the database. No medical data records are available on the card. The user needs either direct access or an access point that is connected to the computer that hosts the centralized database, generally through a network.

U.S. Pat. No. 5,832,488, to Eberhardt discloses storage of a patient's medical history on a smart card. The medical history on the card can be updated, and also stored on a computer database. The card is associated with an ID number, rather than a name, and only health care providers have a list to associate the ID number with a name. The data is not otherwise protected or secure, and there is no mechanism for a patient to selectively authorize a physician access to particular data records saved on the card. In summary, none of these systems provide a database that is portable and easily accessible to both health care providers and patients within an environment that adequately protects the patient's privacy.

These and other prior art systems and methods for providing a medical database, which include server-based storage, low-tech compact disc (CD) formats, or low-memory smart cards, have at least the following limitations. The server-based solutions do not allow off-line access to the data, the low-memory smart cards have very limited storage capability and are generally used only as identification tokens, and CDs are neither easy to use nor flexible enough to handle the necessary security requirements. Other limitations of the prior art include the inability to provide integrated data across multiple providers, the inability for the patient (and the doctor) to have easy access to their own medical data and medical history, and the lack of a standard format where the data can be easily stored in a secure form and "mined".

There is a need, therefore, which is lacking in the prior art for a system and method for providing a storage system and method for providing the secure storage of and hierarchical multi-user access to privatized data on a portable database.

SUMMARY OF THE INVENTION

The present invention, which addresses the needs of the prior art, relates to a system and method for providing the secure storage of and hierarchical multi-user access to privatized data on a portable database. The invention may be applied to numerous applications, including, for example, providing an efficient, cost-effective health care system and patient medical record database or providing a multi-user secure system for the sale or rental of music and/or videos downloaded onto a flash smart card owned by the purchaser.

The present invention provides a method of providing, managing, and accessing a multi-user portable secure database. A database is provided with a secure portion and a non-secure portion. The method includes storing security components for encrypting and decrypting data files in the secure portion and storing encrypted data files in the non-secure portion. The method further includes controlling access to the encrypted data files by assigning an access control matrix to each encrypted data file according to a hierarchical structure. The access control matrix defines access rights of each user to each encrypted data file by assigning a level of access to each type of access. A user requesting access is associated with one of the security components for allowing the requested access and the requested access to one or more of the encrypted data files is allowed in accordance with the access control matrix.

A multi-user system is also provided for storing, updating, and accessing secure data records using a portable database, which includes a secure portion and a non-secure portion. The system includes a data structuring module and an access control module. The data structuring module is configured to embed a hierarchical structure for each user into each secure data record in the portable database. The hierarchical structure identifies each user and allows for assigning access rights to each secure data record. The access control module is configured to embed a security element into each secure data record and to cooperate with a security management module for managing a plurality of security elements associated with a plurality of users and with the data structuring module. The access control module is also configured to assign the access rights for each user to each secure data record and to allow a user access to a secure data record in accordance with the assigned access rights. The non-secure portion of the portable database includes the secure data records and the secure portion includes at least one of the plurality of security elements.

As a result, the present invention provides a method for providing, managing, and accessing a multi-user portable secure database system and a system for storing, updating, and accessing secure encrypted records on a portable database. The system and method provide multi-user access on a hierarchical basis, and a portable database that carries with it all necessary information and security components to enable secure access to authorized users.

The system and method is particularly useful for managing health care data between multiple users including various health care providers, pharmacists, medical insurance companies, and the patient to whom the health care data pertains, and, optionally to those outside the medical community for specific purposes. A "medical smart card" held by doctors, EMT workers, and others also includes patient-controlled access, requiring patient authorization for release of any medical information to the selected third-party.

The preferred embodiments of the method and system for providing the secure storage of and hierarchical multi-user access to privatized data on a portable database as well as other objects, features and advantages of this invention, will be apparent from the following detailed description, which is to be read in conjunction with the accompanying drawings.

BRIEF DESCRIPTION OF THE DRAWINGS

FIG. 2 is table showing the hierarchical tree structure of users assigned to records in the portable secure database.

FIG. 3 is a table showing an access control structure provided to records in the portable secure database.

FIG. 4 is a table showing global access rights assignable to a data record of the portable secure database.

FIG. 5A is a block diagram representing a step in the method of providing the secure portable database, the step including initializing a portable card used as a platform for the secure portable database.

FIG. 5B is a block diagram representing another step in the method, including personalizing the portable card of FIG. 5A.

FIG. 7C is another table showing the hierarchical structure of the portable secure database showing highest level of user with access rights assigned.

DETAILED DESCRIPTION OF THE INVENTION

The present invention provides a system and method for providing a secure database format and access technology oriented towards portability, small footprint, security, and a distributed nature in a public environment, in which multiple users can have varying levels of access to the secure data. The database, which may be provided on a generic database platform, is highly flexible and easy to use, and allows for users to be added on-demand.

The term "data record" is used interchangeably with the term "data file," "data" and "file" herein to mean data in any format which can be stored as a file on a computer, including text, binary, and graphics.

The data stored in the portable database of the present invention may include multiple formats, including any combination of textual, digital images, digital audio and digital video. In addition, the system and method for providing the secure, portable database of the present invention may be utilized across many market segments.

Moreover, the present invention provides a system and method for embedding the security management and access rights to different levels of data in the database itself, which allows for portability of the secure database. Security management includes providing data encryption and digital signatures to ensure data integrity, and to verify an owner of each data record. Therefore, all data records on the portable database are encrypted and signed. The secure database may be maintained on a personalized data card, which may be carried by a user of the database, such as a high storage secure memory card, for example, an X-Mobile card (XMC), which is available from Renesas Technology America, Inc., 450 Holger Way, San Jose, Calif. 95134. Further, no on-line access to any hosts is required for control of the security. Optionally, however, synchronization with a host database or a patient's personal computer, for example, is provided as a means to backup data from the patient's card.

As one particular example, there is an immediate need for providing a secure, portable medical database system, which is compliant with the recent Health Insurance Portability and Accountability Act (HIPAA). The portable database can be stored in a secure, common format and distributed among patients and health care providers. Each patient preferably carries his own medical history on a personalized secure memory card. The entire database including the medical histories of all patients in a health plan, for example, as well as information about all health care providers in the plan may additionally be stored on a secure server.

Figure 1:
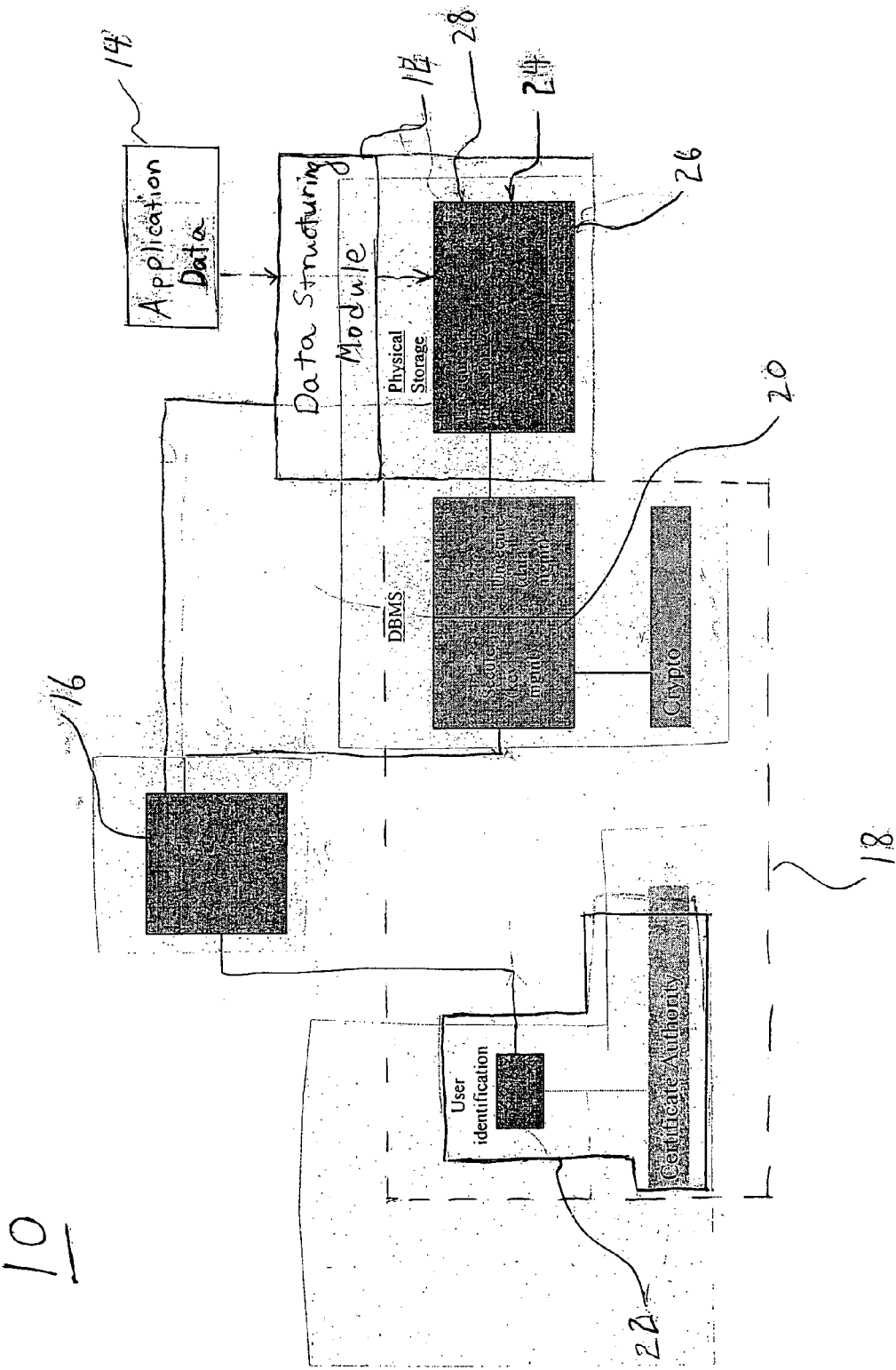
FIG. 1 is a block diagram of a system for providing a portable secure database in accordance with the present invention.

Referring to FIG. 1, the system 10 and method of the present invention for providing a secure, portable database for a particular secure application, e.g., for storing, updating, transporting, and accessing data records, can generally be differentiated into three main functional components: Data Structuring; Access Control; and Security Management. These components are provided in block diagram format. Specifically, the system 10 includes a data structuring module 12 for creating data records from any application data 14, whereby each data record is embedded with a hierarchical structure of users; and an access control module 16, which provides a security layer to the application data 14 by embedding security components and encrypting the data records after structuring by the data structuring module 12. The access control module 16 also provides user interface in cooperation with a security management module 18 to provide a secure portable database in a multi-user environment according to the method of the present invention. Optionally, the system 10 includes the management module 18, which preferably further includes a key management module 20 and a user identification or authentication module 22.

The secure application itself requires some type of physical storage for storing the secure portable database 24. However, the implementation of the system 10 and method according to the present invention function independently from the storage device and are not limited to any one particular type. In addition, any encryption methods known to those skilled in the art may be applied, including both symmetric key encryption, such as Advanced Encryption Standard (AES) and asymmetric key encryption. Examples of preferred physical storage spaces for use with the system and method of the present invention include a flash memory, in which the data can be stored as binary files, or a text based Extensible Markup Language (XML) database.

The database 24 itself is preferably partitioned into a secure portion 26 and a non-secure portion 28. Data records processed by the data structuring module 12 are embedded with security components added by the access control module 16. The resulting encrypted data records are preferably stored in the non-secure portion 28. Also stored in the non-secure portion 28 are encrypted security components and encrypted digital signatures. The non-secure portion 28 may physically be provided by flash memory, e.g., in a flash smart card, or a smart card which has an embedded disk, for example, a Universal Serial Bus (USB) device including flash memory plus processor to handle encryption.

The secure portion 26 contains the security components, which include encryption/decryption keys, certificates, and so on, as described in more detail below. The secure portion 26 is preferably physically provided by a processor, with the security components being made accessible via the access control mode. Smart card technology offers a secure platform for storing and maintaining encryption keys and access control data.

In one embodiment, the digital certificates of all users of the system are stored on each secure data card distributed to the users. Each card also stores the owner's private key stored in a secure portion 26 of the card.

In another embodiment, the public keys may be maintained externally to the portable database, e.g., on a host computer or PDA. These keys would then be accessible, for example, through a card reader operatively connected to the host computer, or through the PDA.

The management module 18 may include any suitable key management and user identification method known in the prior art. The access control module 16 and data structuring module 12 are then configured to cooperate with the management module 18 to provide a secure multi-user portable database. Each of these three modules and its implementation according to the methods of the present invention is described in more detail below.

Referring still to FIG. 1, a method of the present invention includes providing and managing a portable secure database 24, which includes providing the database 24 with the secure portion 26 and the non-secure portion 28. The method further includes storing security components for encrypting and decrypting data files in the secure portion 26, and storing encrypted data files in the non-secure portion 28. The method may further include storing encrypted security components in the non-secure portion 28. Security components may include keys and certificates associated with each user. As is well-known to those skilled in the art, the certificate contains a public key associated with the owner of the certificate. In addition, the certificate is preferably digitally signed, for example, by a Certificate Authority or a Card Administrator (CA). Therefore, a CA public key may be used to validate the public key of the owner of a data record from his certificate and identify the groups associated with the owner, according to methods well-known to those skilled in the art.

Figure 7A:
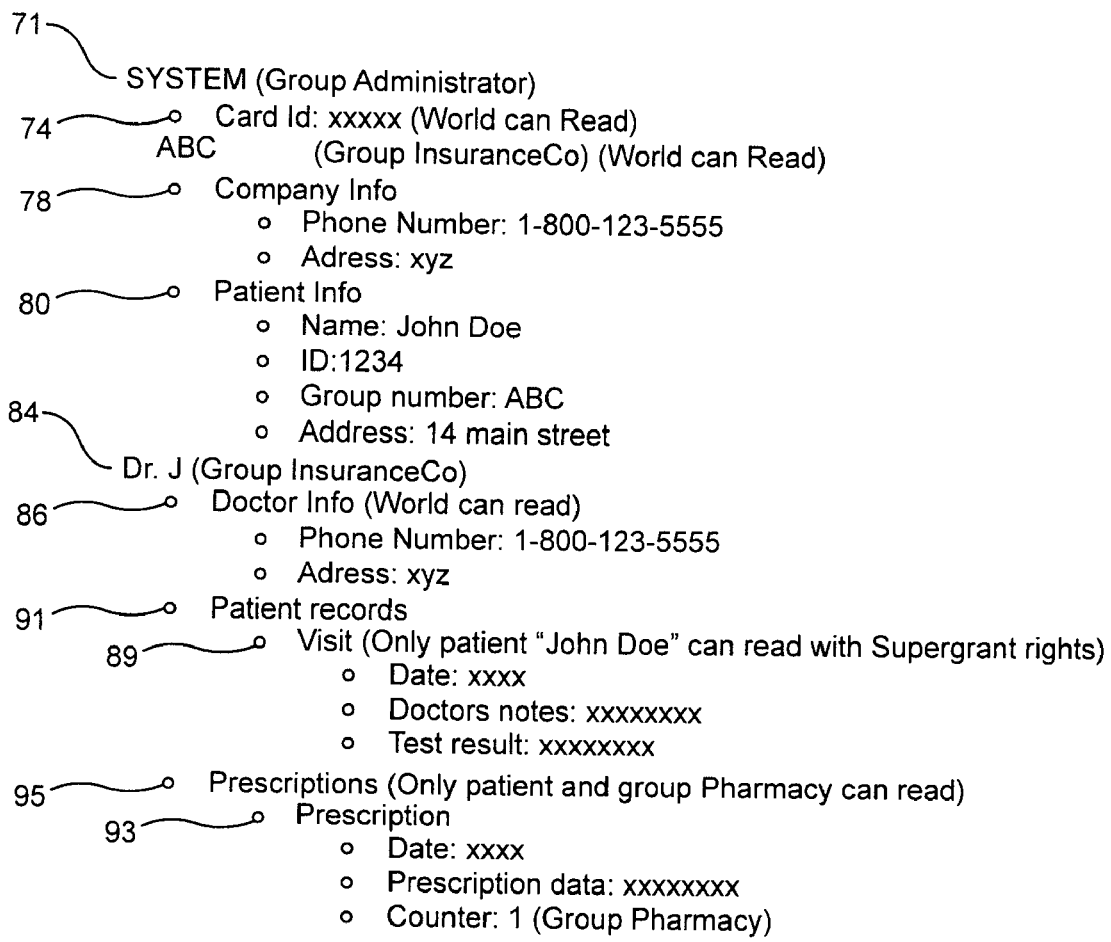
FIG. 7A is a representation of contents of the portable secure database after the steps described in FIGS. 5A, 5B, and 6, and after a visit to a pharmacist.
Figure 7B:
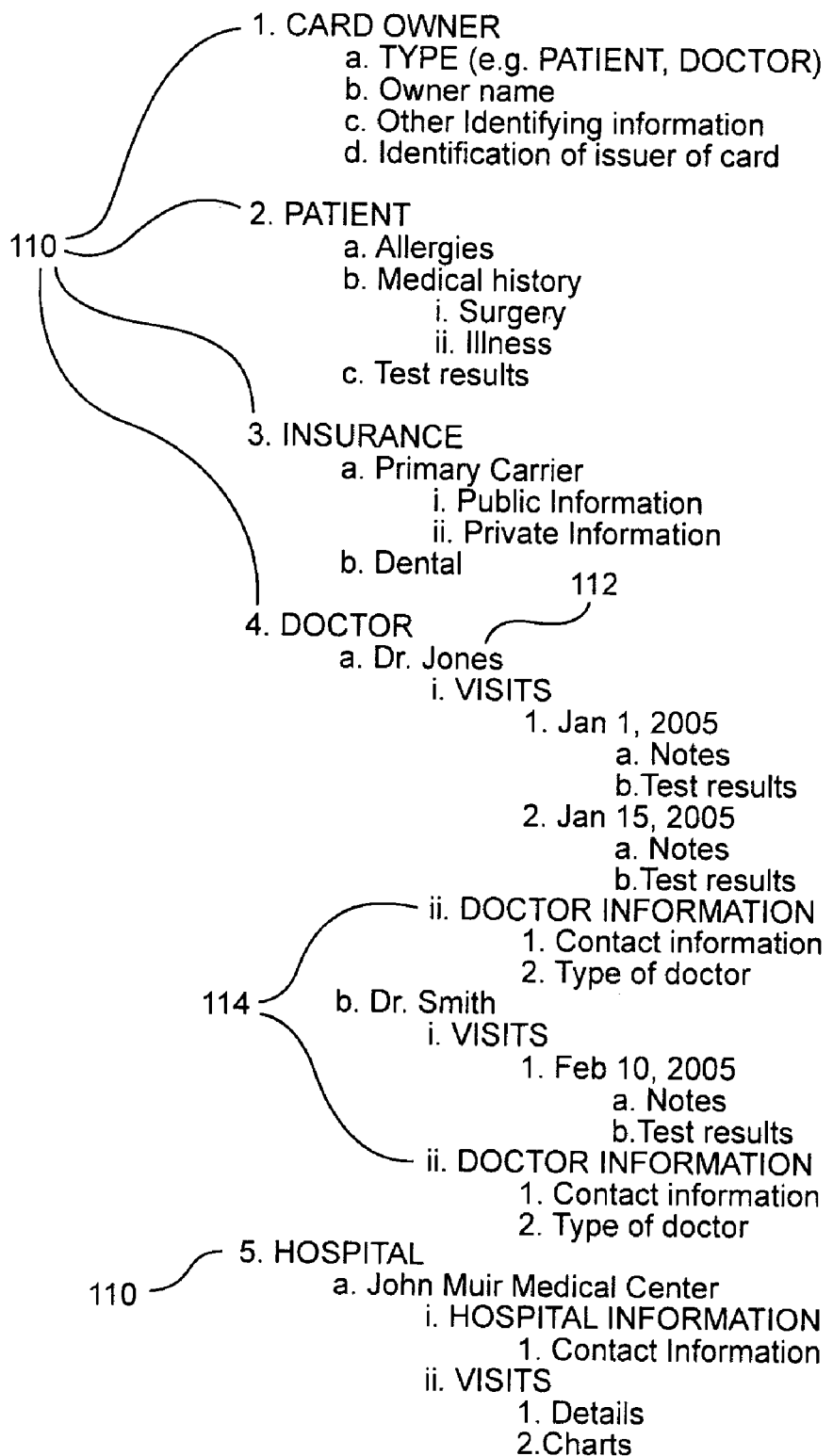
FIG. 7B illustrates the hierarchical structure of a portable secure database formed in accordance with the present invention.

Access to the encrypted data files is controlled through the access control module 16 by assigning a level of access available to each encrypted data file/record according to a hierarchical structure of users (see FIG. 7B for representation of hierarchical structure). Preferably, the user identification module 22 identifies the user requesting access. The access control module 16 then associates the user with one of the keys stored in the secure portion, which is needed for decrypting the requested encrypted data files. If the level of access associated with the requested file for the user requesting access is allowed, the appropriate key is applied to decrypt the requested encrypted data files, and to ensure the integrity of the data, for example, by verifying that originally-stored data has not been modified.

The identity of each user, including an ID, is embedded in a certificate, which is initially obtained for each user of the system from, for example, the card administrator of the database application. The user's membership in one or more groups is also identified using cascading certificates issued from the secure portion 26 of the database 28 (see FIG. 1). The certificates attest to the user's identity and membership in a group (e.g., Emergency Medical team (EMT) worker, or hospital administrator) and affect each user's access rights.

The certificates are stored in the non-secure portion 24 of the database 28. The identity as defined by the certificates is used for all interaction with the portable database 28, including, but not limited to, the authentication of a user logging in. Upon authentication, the user's certificate, as well as cascading certificates attesting to the user's membership in different groups are accessed.

The user identification module 22 operates to authenticate and verify a user requesting access by any means known to those skilled in the art, including any one of several clearly designed security mechanisms, e.g., challenge and response via digital signature verification. Upon verification, the user requesting access is identified with the corresponding certificates. The key requirement is that a well established interface be used to store the private key on a protected user device such as a smart card or an XMC, which is a product having a flash memory Security Disk (SD)/Multimedia Card (MMC) with an embedded smart card chip. Examples of known security token interfaces include Cryptographic Application Program Interface (CAPI) and Public Key Cryptographic Standard 11 (PKCS11).

The private key associated with the certificate identifying the owner of, for example, the flash smart card, is maintained in the secure portion 26 of the database 28 and is accessed from the secure portion 26 upon authentication of the user. The private key, which is stored in the secure portion 26, is never released but is used to execute standard cryptographic operations such as digital signature generation and decryption of keys, in accordance with methods well known to those skilled in the art.

The data structuring module 12 in cooperation with the management module 18 operates to create and maintain a hierarchical tree structure used to represent all data and users in the database, which is embedded in the directory structure of the database. Through use of the hierarchical tree structure, the data is added to the database into a particular folder owned by the user in a seamless, automated, and secure manner. All data in the owner's folder occupies a branch of the hierarchical tree, and the owner has control over all data in his/her branch, with some possible exceptions. All data is preferably encrypted and the files can only be viewed and accessed by the parties specified through the access control module. In addition, all data is preferably digitally signed using the private key of the entity or individual creating the record file. The digital signature contains details of the creator, i.e., the owner of the data, which can be viewed concurrently with the data itself. Data can also be marked as write-once, so that the data cannot be changed. In one embodiment, the signed data records cannot be altered later, even by the creator.

In addition, a mechanism for determining any data in the database that has been tampered with is also provided. For example, a signed audit log or "hash" as known to those skilled in the art is preferably created for all records as they are inserted into the database. An on-going hash of this log may then be rehashed and signed with the card administrator's key to insure that the records have not been tampered with.

The access control module 16 in cooperation with the data structuring module 12 provides and maintains an access control structure for assigning and monitoring individual access rights to each data record. For example, the access control module 16 provides the ability to specify who can read the data (an individual or group, where the group is defined by the entity issuing the certificates), and allows a mechanism for a user who has the proper access rights to read the data, and to grant those access rights to the data to someone else. In addition, the format for assigning security and access rights is provided independently of the database platform, such that the physical database itself does not have to have security built in. The structuring module 12 allows the capability for a record to be exported from the database 28, to be imported into another database, or to be used as a standalone record. Exported records have the same format as records in the database. A method of exporting a data record from the portable database, therefore, may include exporting either a read-only copy, a read/write copy where the original is locked and cannot be changed if is re-imported, or a read/write copy, where the original is not locked.

In a system for maintaining a database, reliable, trusted timestamps are difficult to maintain because the timestamp must be retrieved from a secure server, which generally requires the user to be online. According to the method and system of the present invention for providing a portable secure database, an additional digitally signed record may be attached to each encrypted data record by the access control module 16 to allow access rights to be granted to a record for a limited time only.

These features are obtained in part by providing a particular simple record format for all data, which is tailored for a micro/portable database. As described above, the portable database may be physically stored on devices such as flash memory smart cards, with the secure portion provided by a processor running the access control module and the non-secure portion provided by flash memory.

As described in more detail below, the system 10 provides a method for all operations on the data records to be done automatically each time in a clearly specified, simple format. The system and method of the present invention is further described by way of example in terms of a preferred application of the portable database to the management of patient medical data. However, the scope of the present invention is not intended to be limited to medical data, having application to any use requiring a multi-user secure portable database. Such other applications may include, but are not limited to, digital media such as music and/or videos, retail loyalty cards, maintenance records for aircraft and automobiles, and secure access and payment cards, for example, for school campus environments.

Referring to FIG. 2, the data structuring module 14 provides a hierarchical tree structure of ownership to represent all data. The hierarchical structure is shown for one item or data record 30 in the tree. Each record 30 contains a name and a value, and represents either a folder or a tree end node (i.e., contains data). The data can be in any format which is able to be stored as a file on a computer, including text, binary, and graphics. An indicator well-known to those skilled in the art, such as Multipurpose Internet Mail Extensions (MIME), preferably indicates the data type. File extensions can be used as well to name the file and to give identity to the file type.

The first level (last row) 32 in the hierarchical structure of each record 30 indicates an individual or entity. That entity controls all data within its tree; in other words, the data records "owned" by a particular entity can be created, read, updated, or in some cases deleted by the owner of the data. The individual may be, for example, a particular insurance company, identified by a particular User Identification ("User ID") 34.

Each individual user 34, as identified in the first level 32, is one of the users of the database system. A "user" as the term is referred to herein, refers generally to any card holder, data record owner, or third-party user of the database of the present invention.

Each user of data is also a member of a group 36 in a second level 38 of the tree, as identified in each user's certificate, which allows the various owners of data records to be categorized more generally, e.g., as an insurance company, a doctor, an emergency medical team (EMT) worker, a pharmacist, or a patient. Each user is additionally often associated with a second group more particularly identified, for example, a particular doctors' group, a specific insurance company, and so on. Every owner 34, as well as third-party users who do not own any data records in the database, is also a member of the "world" of users 40 at the top of the hierarchical tree. Third-party users may include, for example, those with a one-time or limited-time access, for example, summer camps and educational institutions requiring physicals, and attorneys representing a patient in a personal injury case. The identity of each user, including the ID, is embedded in the certificate, and the individual user's membership in one or more groups is embedded using cascading certificates issued from the secure portion 26 of the database 28 (see FIG. 1) for attaching to each owner's data records when generated.

In other words, the hierarchical structure 30 is assigned to each data record automatically as it is created via the data structuring module 14 represented in FIG. 1, according to the identity and group membership in the user's associated certificates, which are retrieved upon authentication. By default, the creator of the data record is the owner 34. An owner 34 has permission to control all data within its branch of the hierarchical tree.

Referring still to FIG. 2, the system also includes an access control structure, whereby each item 30 in the tree contains an access control entry which has the same format throughout the database. The access control entry contains a write once flag, which, if set, indicates that the record has been written only once, and has not been deleted or modified. Therefore, if the flag is set, the data record is valid. The access control entry further includes a level of access. The level of access in the access control entry preferably includes one of the following values: Restricted (R), Allowed (A), Grant (G), and Supergrant (S).

Referring to FIG. 3, the access control structure includes an access matrix 50, through which one of the values listed above is assigned to each type of access 52 available (uppermost row), and to each level in the hierarchical structure of the data record 30. The types of access preferably include: Create, Read, Update and Delete. These types of access, as their labels suggest, represent the capability to create, read, update or delete a particular file.

A value of "Restricted" in a particular row and column of the matrix 50, therefore, indicates that the type of access 52 indicated in the column is not allowed to the hierarchical level of users (e.g., individual, group, world) represented by the row in which the value of Restricted is found. Similarly, "Allowed" indicates that the corresponding type of access 52 is allowed to the particular level of users in the hierarchy. The "Grant" level of access includes the Allowed level of access, as well as the permission to grant the Allowed level of access to others. Finally, the value "Supergrant" permits the level of users to which Supergrant is assigned for a particular type of access (e.g., Read, Create, Update or Write) permission to grant either the Allowed or Grant level of access for the particular access type to others.

In the example shown in FIG. 3, world rights are restricted to read-only access. The level of access rights in a level supercedes the rights of any row beneath it in the same column. For example, because the World 40 has read-access as shown in the "Read" column 54, so do the Group(s) 36 and the Individual 34. Therefore, the access rights 56 for the Group(s) 36 and the Individual 34 are granted automatically (as shown by use of parentheses) and are not available for modification.

The Group row 38 indicates the rights for a member of a group to access the data. One or more groups can be put in the Group User ID field 36. In other words, one or more Group records can be created for an item 30, in order to grant different groups different rights.

The individual row 32 similarly indicates the access rights of a particular individual or entity, identified by the User ID 34, to the record 30. The individual 34 is the primary holder of a certificate. In the example of FIG. 3, the record holder 34 of the item 30 has access to create, read, update, and delete the file and is the owner of the data 30.

In a preferred embodiment, the access matrix 50 is automatically generated for each record as it is created, according to the particular user creating the record, as well as the type of record being created. The non-secure portion of the database 28 is preferably partitioned so that different types of records are automatically created in different sub-directories under each user's directory. For example, the access control matrix 50 shown in FIG. 3 is automatically generated for general informational records created in one sub-directory of a patient's main directory in the database. The system automatically assigns the appropriate access rights according to the hierarchical structure of the database. For example, unless otherwise specified, a record created in a particular folder assumes the same access rights as the folder it is created in. Likewise, a folder assumes the same access rights as its parent folder, unless otherwise specified. More private records with, for example, particular information regarding doctor's visits, are maintained in a different sub-directory with more restrictive access to those other than the patient.

The access control structure of the system of the present invention may further include a counter associated with each record. The counter is preferably decremented by another entity, but it may also be decremented directly by a component of the access control module 16, which is embedded in the secure portion 26 only when another specific card is present in the system 10, e.g., a pharmacist's card. For example, when a doctor issues a prescription, the counter indicates the number of times it has been filled. All members of the group "pharmacy" have access to this counter. In a specific example for a prescription providing for no re-fills, the counter would initially be set to one (1). Upon filling the prescription, all group members of pharmacy would decrement the counter on the records in the database pertaining to prescriptions for this patient to zero (0).

The system and database formed in accordance with the present invention also preferably include additional record storage security features. Records are stored according to a common format. All records, except for those that can be read by the World, are encrypted. In addition, the encrypted records may include a local timestamp as described above. The time-stamped record, together with the unique card ID assigned by the administrator, ensures that the record is unique and has not been copied from another card.

Preferably, each encrypted data record includes the timestamp and a digital signature. The digital signature also includes the unique card ID from which the data originated. Data accessible to the World, which is not encrypted, also includes a digital signature.

The method and system of the present invention for providing, managing and accessing a secure portable database is provided herein by way of example for a particular embodiment of a secure portable database for patient health data. Preferably, a data card, such as a flash smart card, is used as a platform for the portable database. The card is preferably initialized by a card administrator. Initialization includes personalizing each card and forcing certain access control rules to always be applied to particular record(s) for all entities or users. Referring to the item 60 shown in FIG. 4, a blank entry 62 in the access control matrix generated by the administrator indicates that the card holder has privilege to assign any access value to the corresponding hierarchical level and type of access.

An individualized card is preferably issued for each user of the database. With reference to FIG. 5A as well as to FIG. 7A, each card is first initialized 70 by assigning a unique card ID number. Preferably, a card administrator (CA) creates 72 a folder, e.g., "SYSTEM" 71, on the card for the entity CA, where the CA is a member of the group "administrator" (ADM). The CA then assigns an ID number to the card holder, which will be used to identify both the card and the card holder or owner, and creates 74 a file in the SYSTEM folder that contains the card ID number. An access control matrix 76 is automatically assigned as shown in FIG. 5A to the card ID file, granting READ access to all users in the hierarchy (to World), but full access only to the CA. A certificate and private key (protected by a PIN and/or biometric data such as a fingerprint scan) will also be issued to the card holder as part of this process. These are used to identify the owner, and to encrypt and sign all data records.

Multiple portable data cards are generated in this manner and distributed, for example, to an insurance company for issue to individual patients who will own the card. Referring to FIG. 5B and still also to FIG. 7A, the insurance company, e.g., "ABC", creates its folder 78 on the card issued according to FIG. 5A and preferably creates file(s) 80 in the folder containing records such as patient identification data, including name, address, and preferably, the patient's insurance ID number and group number. Alternatively, however, the same files can be created by the CA and stored under the SYSTEM folder 71 as shown in FIG. 7A. Upon creation, the access matrix is automatically assigned 82, as before, preferably to give read rights to the WORLD, and full access rights only to ABC company. It may also be preferable to assign a Supergrant access level to an insurance company (e.g., ABC) for files created in its folder. The access rights and information on the card could then be updated and passed on easily to a different insurance carrier, should the patient change plans.

Other data may also be included in this or other files, which will be readable by the WORLD, including any combination of date of birth, social security number, a photograph, religious preferences, driver's license, etc. This data may also include a card owner's wishes to be an organ donor, and special medical conditions, such as allergies.

Figure 6:
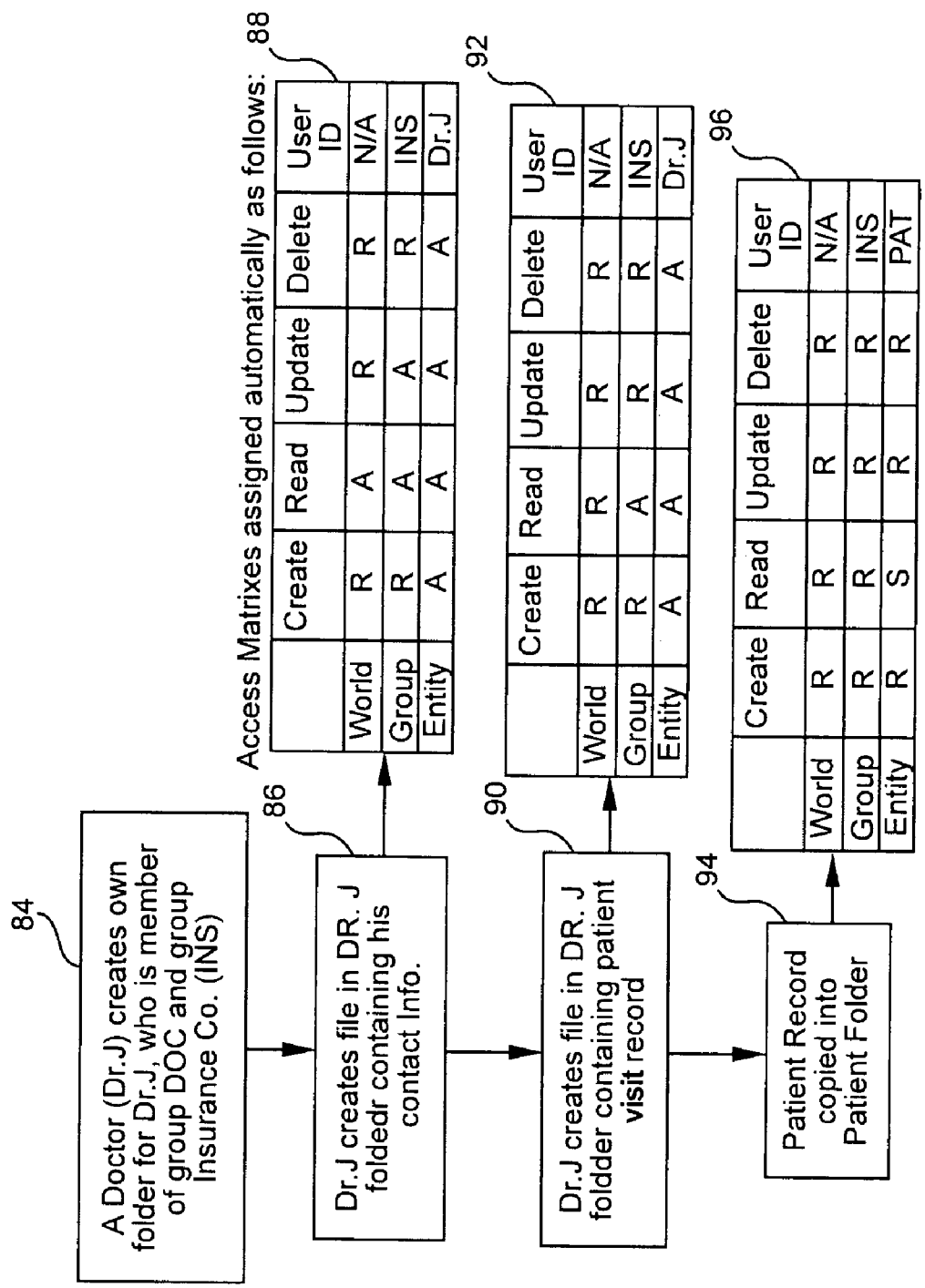
FIG. 6 is a block diagram representing further steps for providing the portable secure database of FIG. 5A for patient health data, including creating access rights to patient medical records created in the portable secure database.

Referring to FIG. 6 and still to FIG. 7A, the portable database is updated in this example every time the patient sees a physician for medical treatment. First, the physician creates his own folder 84 and files within the folder. The physician, e.g., "Dr. J," creates a physician information file 86, which the world can read, containing his contact information. The file is again automatically assigned access rights 88 automatically, with the group INS, representing the patient's insurance company, having only read and update access rights to the doctor's informational files.

The portable database is then further updated with one or more files 89 containing the results of the doctor's visit. The files may include text files, as well as image files, for example, X-ray data, and/or audio and video files, e.g., volume renderings of three-dimensional computer assisted tomography (CAT) scans or magnetic resonance imaging (MRI) scans. According to the method of the present invention, a copy of the patient records 91 may be created 90 in the patient's sub-folder within the doctor's folder, with an access control structure automatically generated 92 with full access rights granted only to the doctor (Dr. J) at a level of access of Allowed to create, read, delete and update the file, and optionally, with READ only access granted to the insurance company. In another preferred embodiment, once the file is created and exited, the doctor only has READ access to the file; i.e., a write-once flag is enabled, which locks the file and helps prevent tampering. The doctor, however, may review all of his previous records of this patient at any time.

A copy of the patient (PAT) records may also be created 94 in the patient PAT's folder, with an access control matrix 96 assigning Supergrant privileges to the patient to grant READ access to others, e.g., to another doctor, and/or to his insurance company. Alternatively, because each individual doctor is also a member of the group "DOCTOR," the patient may grant read access to the group "DOCTOR" to allow any physician total access to all of his medical records.

Therefore, upon transporting the portable database to a different physician, the patient can grant access to the second physician to read the results of the previous visit to a different doctor. The means by which such authorization is provided includes exporting data using the public key of the intended recipient.

A file may also be created in the patient's directory, which includes any data which may be useful for the patient to have publicly available to certain users with access to the database, without comprising privacy rights, such as: blood type, allergies to medication and other materials, special health conditions, e.g., epilepsy, diabetes, heart conditions, the existence of metal objects and pace makers, and other special medical conditions. Such information might include important patient history information that an emergency medical team (EMT) worker could quickly access in the event of an emergency. Preferably, a patient's general physician would create such file in an EMT directory, for example, which would have full access rights to the general physician, and read access to the world. In addition, new emergency records could be written to a patient's card during transport to the hospital including vital signs, blood pressure, and other medical data collected during emergency treatment. Such data could then be accessed quickly by physicians at the hospital.

The portable database on each patient's card is thus updated, transported from one health care provider to another, and accessed upon permission of the patient. The database may also be updated by a pharmacy when the patient has a prescription filled. The prescription may be added to the card by the doctor, granting read access rights to the entire group "pharmacy." In this case, a particular pharmacist within the group merely searches the card for a keyword, for example, "prescriptions" to locate and read the prescription 93 entered by a doctor under his prescriptions folder 95. Optionally, the prescription may be hand-delivered by paper prescription. In either case, the database should be updated by adding or updating the prescription information, including decrementing a counter on the card if the prescription to keep track of refills.

An example of the contents of the secure portable database on the card after the patient fills his prescription at the pharmacy are provided in FIG. 7A. A security layer has been added to the records as described above, so that the patient can carry his own medical report and can view his own medical records and history securely, for example, on a home personal computer or on a personal digital assistant (PDA) or other reader adapted to read the card, e.g., a smart card with flash memory, without risk of altering or damaging the records. For additional security, a central database may be provided so that the patient, as well as health care providers, can back up all records into the appropriate folders on a physical storage device, which is preferably accessible to the Internet. The central database will maintain the same level of security to the files as the portable database, since the security components are embedded in the files themselves. The backups could be done every time the card is written to, or according to a pre-arranged timed interval.

Because the patient has Supergrant access to his or her patient records, the patient can authorize and consent to particular records of his choosing to be read by another select individual, e.g., another doctor. He may also choose to send any of the encrypted medical records to an individual securely via the Internet or e-mail.

FIG. 7B provides another representation of a hierarchical structure provided to a secure portable database formed in accordance with the present invention. The database is partitioned first according to the groups, Card Owner, Patient, Insurance, Doctor, and Hospital. Subdirectories are created under each group. It can be appreciated from this structure that an access control matrix can be defined for each sub-category representing different types of information, allowing the access control rights to be automatically assigned upon creation of a data record according to the hierarchical structure. For example, "Dr. Jones" may have full access to all files within the Doctor's directory 112, while the World has only Read access to files within Doctor Information 114, and only a patient has any kind of access to his own medical records 116 at a Supergrant level of access. The particular structure shown in FIG. 7B is one possible representation to which the scope of the present invention is not meant to be limited. One can appreciate different ways to structure the database to accomplish the same purpose, e.g., having different or more main directories, and/or adding patient sub-directories under each Doctor's directory. In addition, individuals may be a member of more than one group, and thus an owner of a card may have subdirectories under more than one main directory.

FIG. 7C provides another representation of the hierarchical structure of the database showing an example of how access rights are assigned to different files within the hierarchical structure of users. The owners of each directory and the data records contained therein are shown in the left column 120. A description of the data records that may be included in each directory is provided in the second column 122. The access rights to the record are then described for different types of access in columns three through six, CREATE 124, READ 126, UPDATE 128 and DELETE 130, respectively, by listing the highest level of user granted the particular type of access. For example, a patient's social security number 132 is readable by the WORLD, but can only be created, updated or deleted by the Owner (of the directory), i.e., the patient. In another example, test results 134 generated by a particular doctor may be read by the patient as well as the Owner, the doctor, but may not be deleted by anyone and can only be created or updated by the Owner, the doctor.

As already described, the creator of a record is automatically an owner of the record and is signed by the owner. However, one may also assign ownership rights to another. For example, a patient may provide rights to some of their data for research. In addition, in some cases, for a user other than the owner to gain a particular access level, the presence and authentication of the owner is required. The symbol "/O" after a level of user listed in FIG. 7c indicates such a case. For example, READ and CREATE in medical history 136 under the patient's directory, indicate that the patient must be present and authenticated in order for the indicated second user, an EMT worker and doctor, and a doctor to have READ and CREATE access respectively.

Access to the portable database and authentication is physically provided using any device that includes a processor on which the methods of the present invention may be processed, and which may be operatively connected to the portable database as needed. For example, any computer, e.g., desk top, portable, or other, or a suitable PDA may be used. The processing device preferably runs a standard set of features, preferably through a graphical user interface (GUI), to allow easy access to the card and automatic implementation of the security. In addition, at least the management module 18 preferably runs on the computer, by accessing the security components stored in the secure portion 26 of the database 24 (see FIG. 1).

The interface between the processing device and the portable secure database may be any interface that works with a variety of media, e.g., flash card, hard disk, or the internet. Preferably, the interface is provided by an Application Programming Interface (API) or Extensible Markup Language (XML). In addition, the secure portion of the portable database is preferably embedded with a certificate that ensures the application using the interface is connected to a legitimate database with the expected secure access. Additional secure interfacing and synchronization with other media, e.g., a central database or another card for backing up the portable database is likewise ensured via use of the embedded certificate.

Figure 8A:
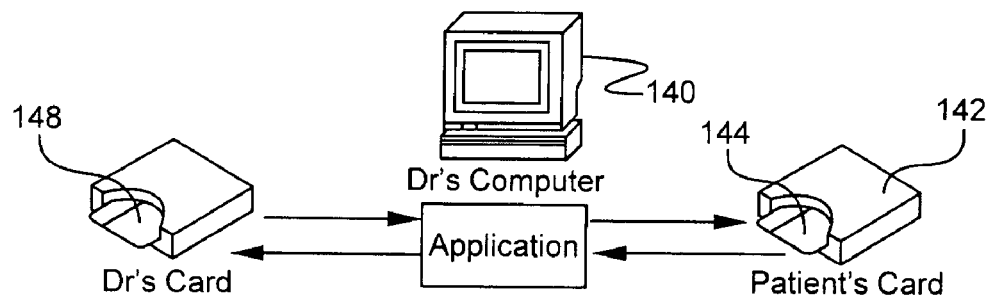
FIG. 8A is a system diagram of a setup allowing access to the portable secure database.
Figure 8B:
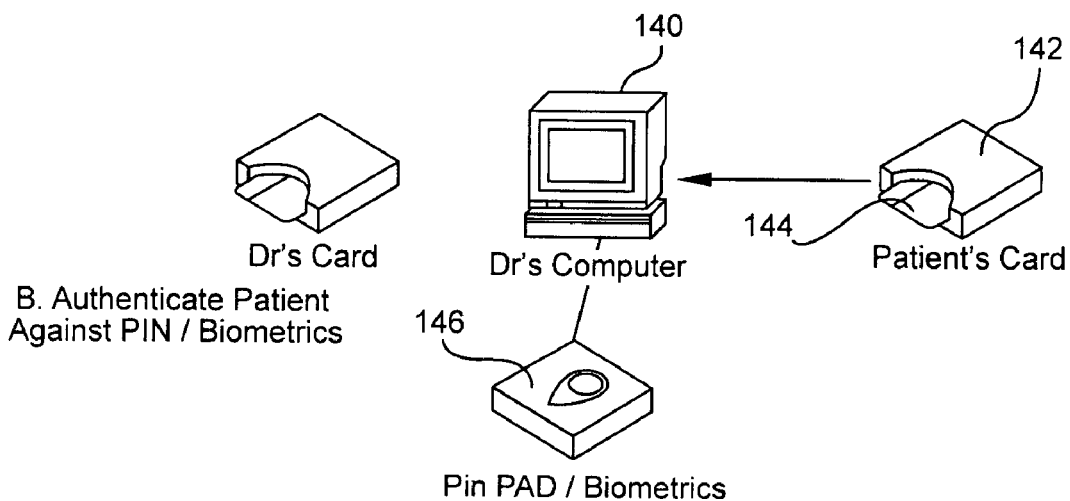
FIG. 8B is a system diagram for authenticating a user requesting access to the portable secure database according to an embodiment of the system and method of the present invention.

Referring to FIGS. 8A and 8B as well as FIG. 1, the user identification module 22 of the management module 18 provides authentication of a user of the portable database 24 preferably using two factors of identification. In the particular embodiment shown, user interface to the database is provided by a computer 140, which is operatively connected to at least one portable database reader 142. The authentication is provided, for example, as shown in FIG. 8B, by the presence of a verified user's (patient, e.g.) card 144 in the smart card reader 142 along with entry of a personal identification number (PIN) known only to the owner of the card 144. Optionally, entry of a biometric identifier 146, such as a fingerprint, rather than a PIN or password may be used.

Referring again to FIG. 8A, preferably, data records created by another, e.g., a doctor, can be written to a user's such as a patient's card 144 only after authentication of the doctor's card 148 against the patient's. This authentication process preferably requires the patient to be present and interactively enter his/her password, PIN, etc., as a means of giving permission to the doctor to read from and/or write to the patient's card. In addition, the doctor also preferably goes through a two-factor identification, so that both doctor and patient are logged on to the application accessing the portable database. However, a computer in the doctor's office may optionally have one authentication factor in the way of either a physical or software key in the computer and the second a PIN, e.g., entered into the computer. Also, the doctor's files may be stored on the computer rather than (or in addition to) on a card.

Figure 9:
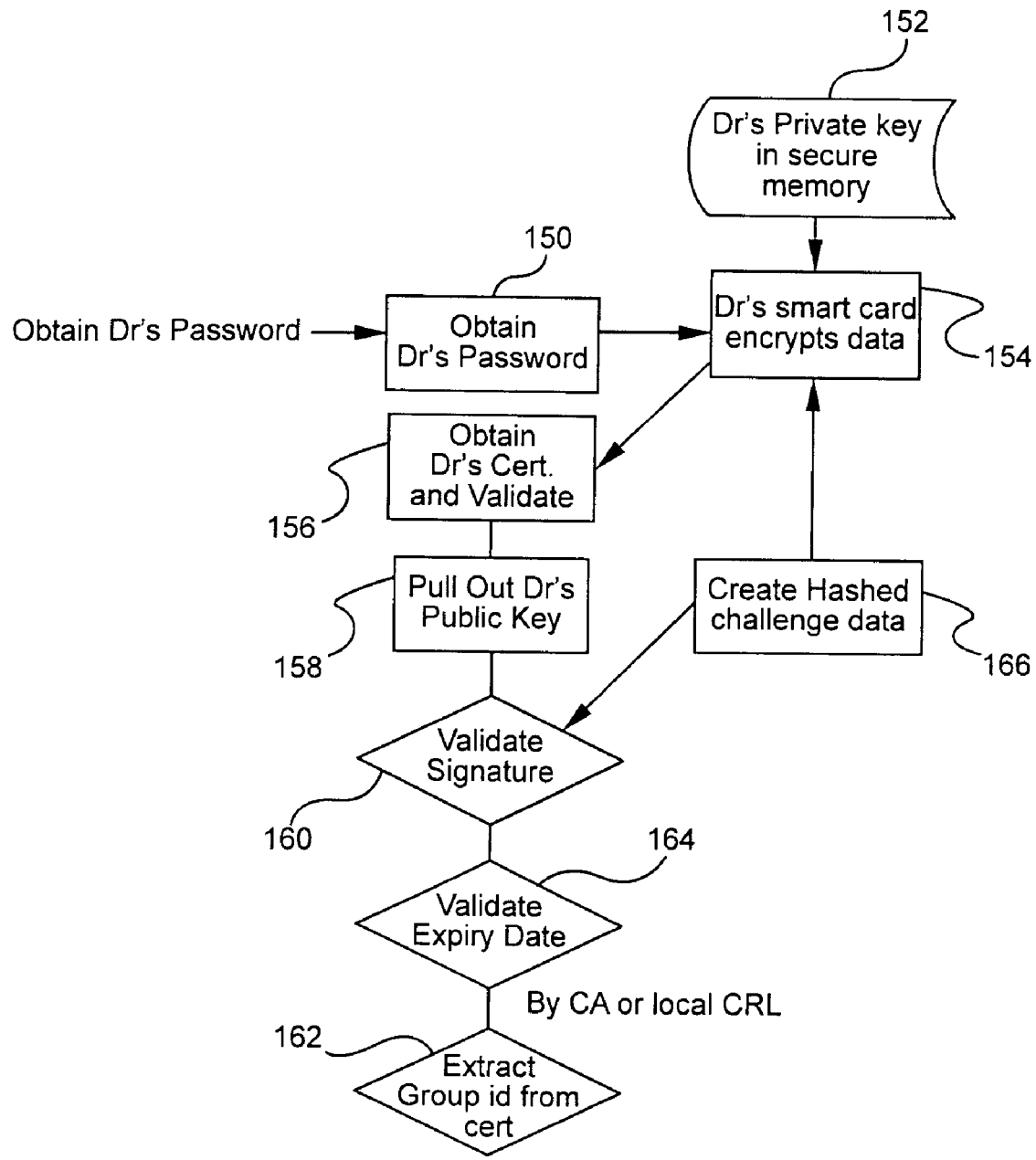
FIG. 9 is a flow diagram of a method of validating a user requesting access to the portable secure database.

Referring to FIG. 9, a method for validating or authenticating a user requesting access is provided for the example of a doctor logging in to the system. The password or PIN entered during authentication (see FIG. 8B) is obtained 150 and used to access a private key 152 associated with the doctor, which is stored in the secure portion of the database. The application sends a challenge 166 to the doctor's card, which uses the private key 152 to sign the data 154. The user's public key pulled from the certificate 158 is used by the application to validate the doctor's response to the challenge 160 and thus validate the doctor's identity within the database hierarchy.

This method may also include validating an expiration date 164 against a remote Certificate Authority or local revocation list. This may be done by comparing the data inside the certificate with a trusted time stamp on-line server.

Figure 10A:
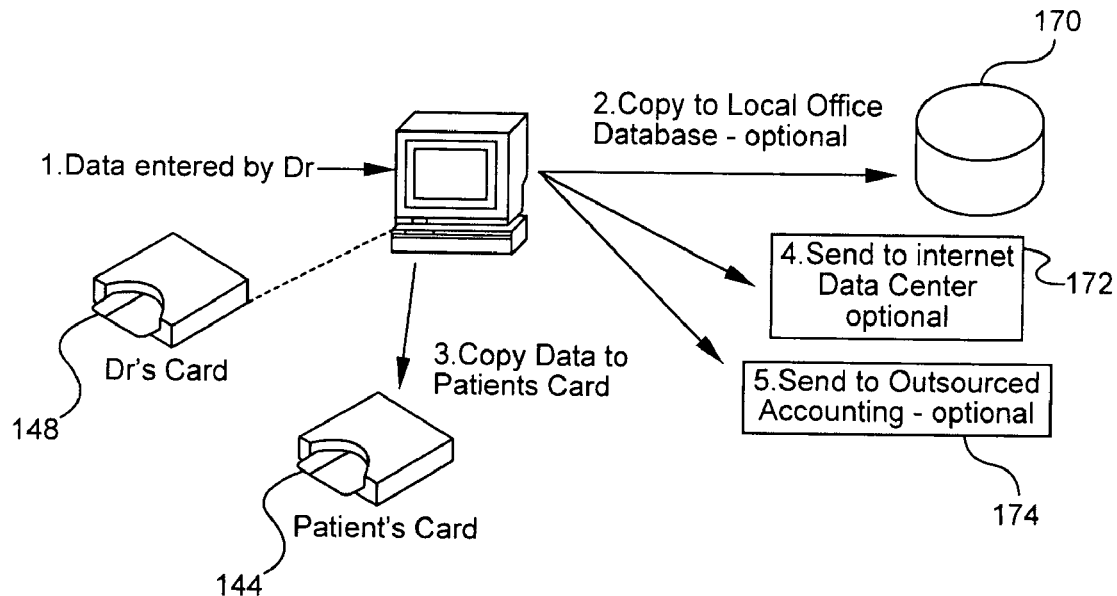
FIG. 10A is a system diagram for writing to a smart card used as a platform for the portable secure database.
Figure 10B:
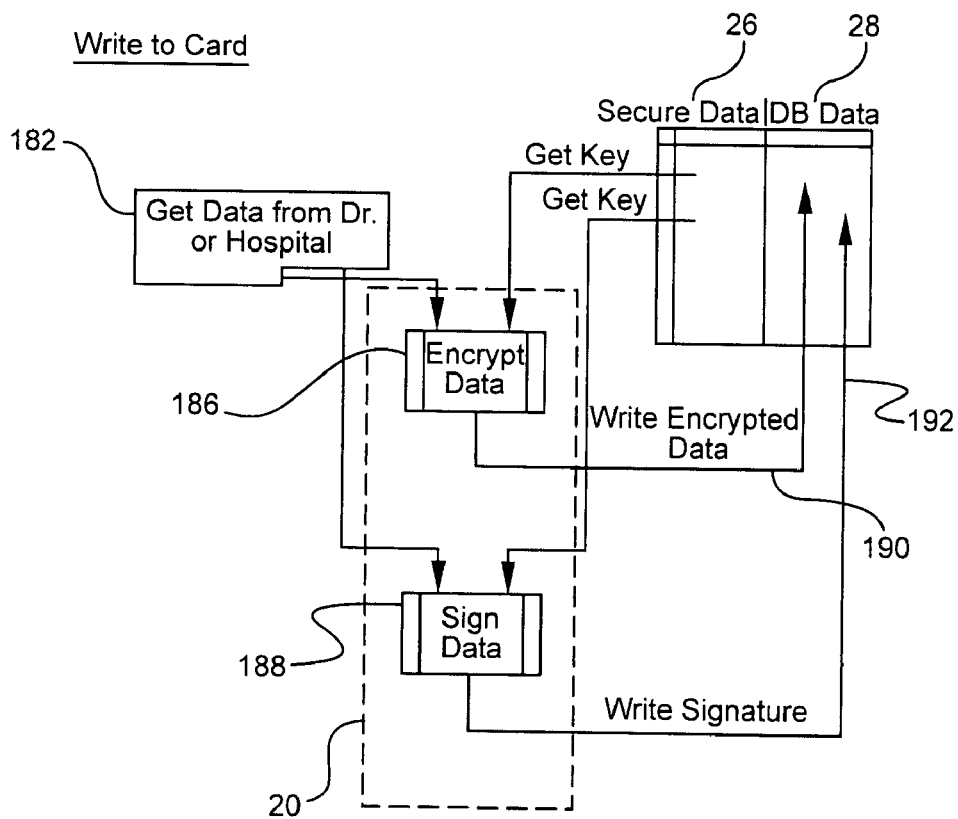
FIG. 10B is a schematic of a method of the present invention for writing encrypted data records to the portable secure database.
Figure 10C:
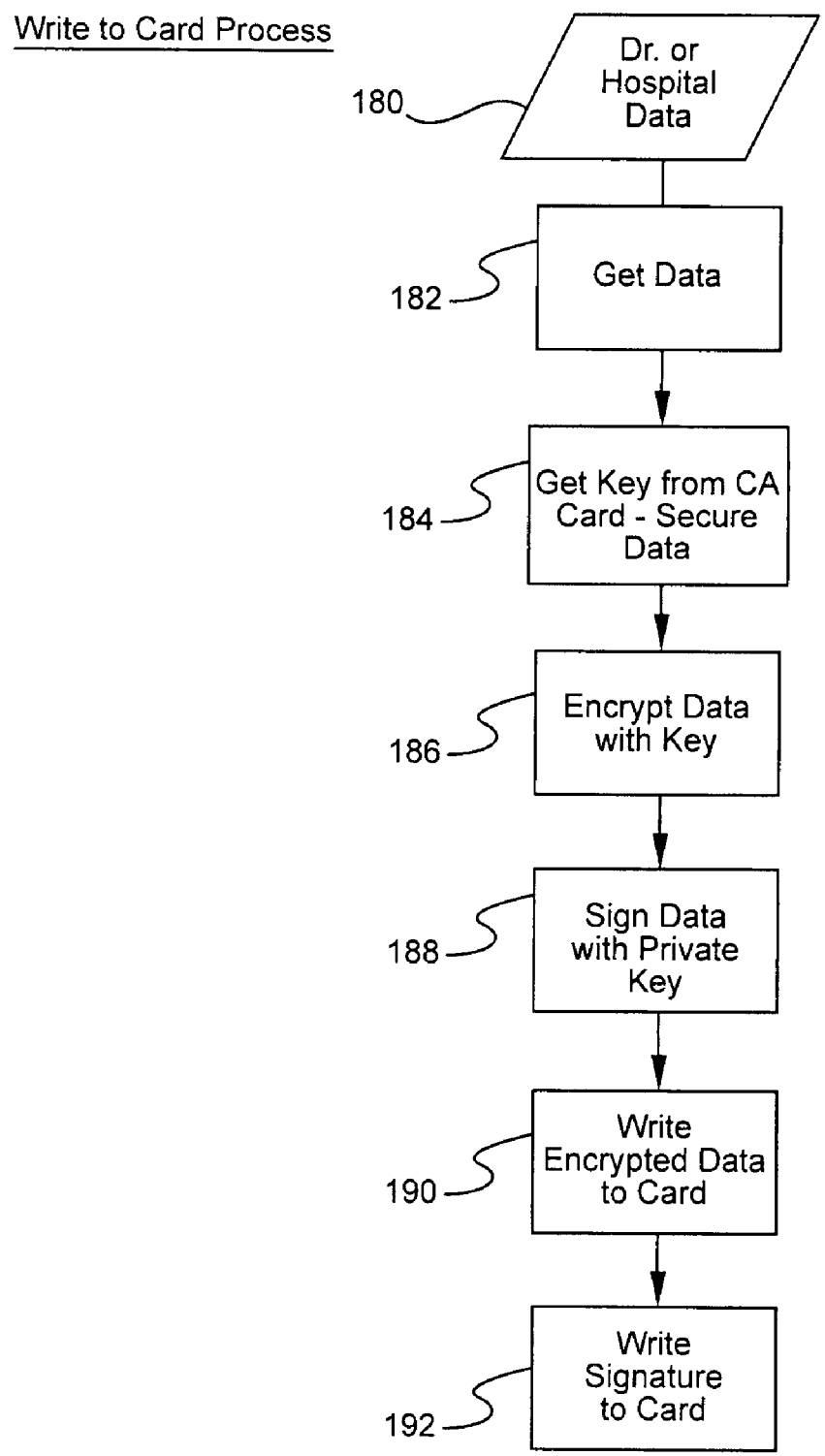
FIG. 10C is a flow diagram of the method of FIG. 10B.

Referring to FIGS. 10A, 10B, and 10C, the system and method of the present invention provide for automatically encrypting each data record upon creation, in cooperation with the key management module 20 of the management module 18 (see also FIG. 1). In FIG. 10A, for example, after authentication and identification/validation, as described above, a doctor may write data records from an office visit, for example, to the patient's card 144. Optionally, the data records may also be exported with the same embedded security components to a local 170 and/or remote backup storage space 172, and parts of the data records containing information regarding the patient's visit, e.g., accounting information, may be exported to a different database 174.

A method of writing to another's smart flash card includes automatically encrypting the data as provided in FIG. 10C, using the key management module 20 as shown in FIG. 10B. In this example, a doctor is writing to a patient's card 144. Referring to both FIG. 10B and FIG. 10C, once permission is granted by the patient according to the authentication and validation processes described above, the data 180 is obtained 182 for writing to the card. A public key is obtained 184 from the secure portion 26 of the portable database on the patient's smart card 144. The data records 180 being copied may, for example, be encrypted 186 with a symmetric key (e.g., Advanced Encryption Standard (AES)). That AES key is then encrypted with the public key of anybody who has access other than WORLD, as determined by the access control matrix assigned to the data record.

Preferably, the doctor's digital signature is also provided to verify its origin. Data is signed 188 with the doctor's private key accessed from the secure portion of the doctor's card. The encrypted data is then written 190 to the non-secure portion 28 of the patient's card 144 along with the attached digital signature 192.

Figure 11A:
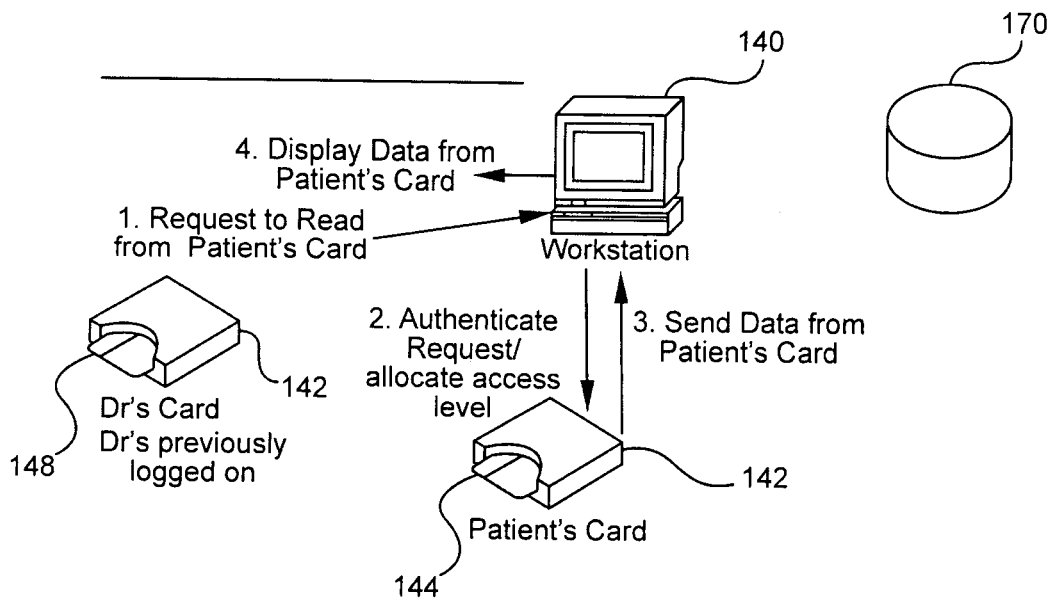
FIG. 11A is a system diagram of a setup allowing read access to the portable secure database.
Figure 11B:
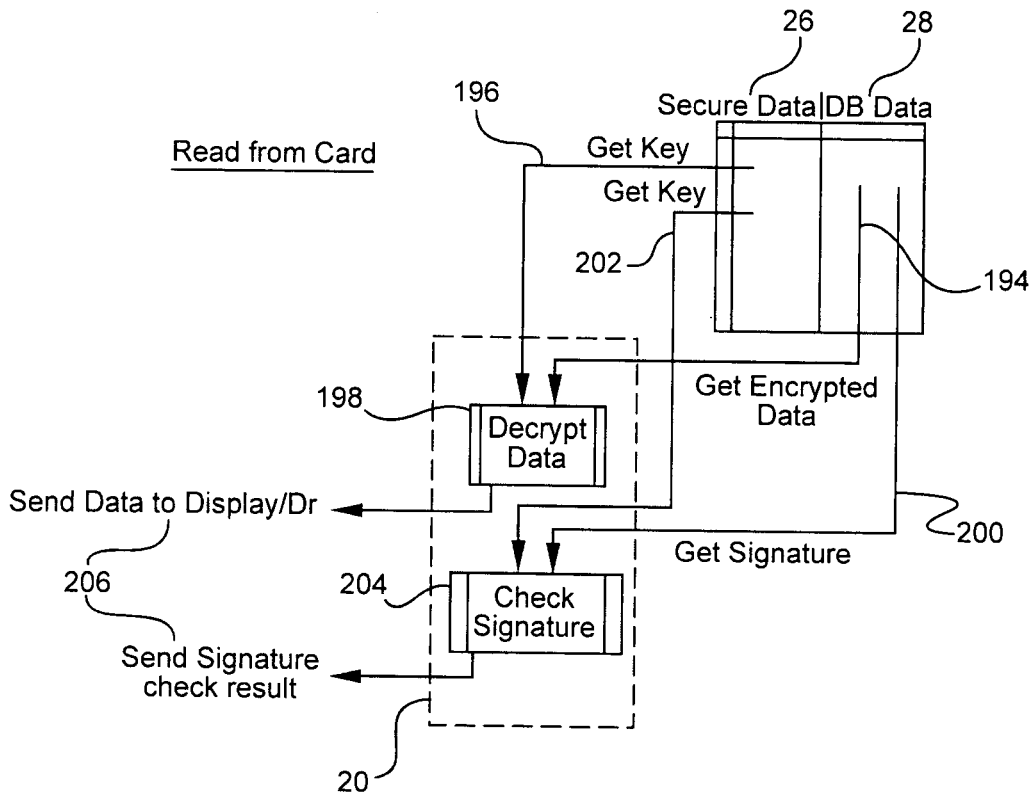
FIG. 11B is a schematic of a method of the present invention for reading encrypted data records from the portable secure database.

Referring to FIGS. 11A and 11B, a method of reading encrypted data records from the portable secure database on the card includes using the key management module 20. The method includes obtaining 194 the encrypted data from the non-secure potion 28 of the database, and accessing 196 a private key from the secure portion 26 of the portable database to decrypt 198 the symmetric key used to encrypt the data records. The method also preferably includes accessing 200 the digital signature attached to the encrypted data records, obtaining the certificate (which includes the public key) of the entity who signed the data, and validating 204 the signature. The results of the signature check, along with the unencrypted data records are preferably sent 206 to a display screen associated with a computer or PDA running the application.

Any method of encryption and decryption known in the art may be used with the methods of the present invention. One embodiment of a method for encrypting patient medical data records 210, for example, for secure storage to the portable non-secure memory is described by FIG. 12, where the interface application runs on a Doctor's personal computer (PC). The method includes the application randomly generating 212 an Advance Encryption Standard (AES) key. The patient data record is then encrypted 214 with the key along with the group ID(s) access information obtained 216 from the access control matrix. The encrypted data is then saved and stored in open (non-secure) memory 218. In addition, the application also encrypts the AES 220 with the patient public key obtained 222 from the secure portion of the smart card and stores the encrypted AES in open memory 224.

The encrypted data record 225 may then be accessed, decrypted and sent to the entity with the access rights to at least read the data. After the two-factor authentication validates the user (e.g., patient) requesting access, at least one of the factors is used to begin the decryption process. For example, a password or PIN 226 entered during authentication (see FIG. 8B) is sent to a secure memory engine, e.g., smart card, for verification. In response to the verification, the encrypted AES key 228 is obtained 230 from the open flash memory and the patient's private key, which is stored in the secure portion, is sent 230 to the smart card. The AES key is then decrypted 232 using the private key. The decrypted or open AES key is then applied automatically to decrypt 234 the patient data. Access to the decrypted data is then made available 236 according to the access rights assigned through the access control matrix for the user requesting access. Other examples of encryption/decryption techniques are provided below. It is understood, however, that these examples are not intended to limit the scope of the invention and any cryptographic method appropriate for use with the secure portable database may be used.

Figure 12:
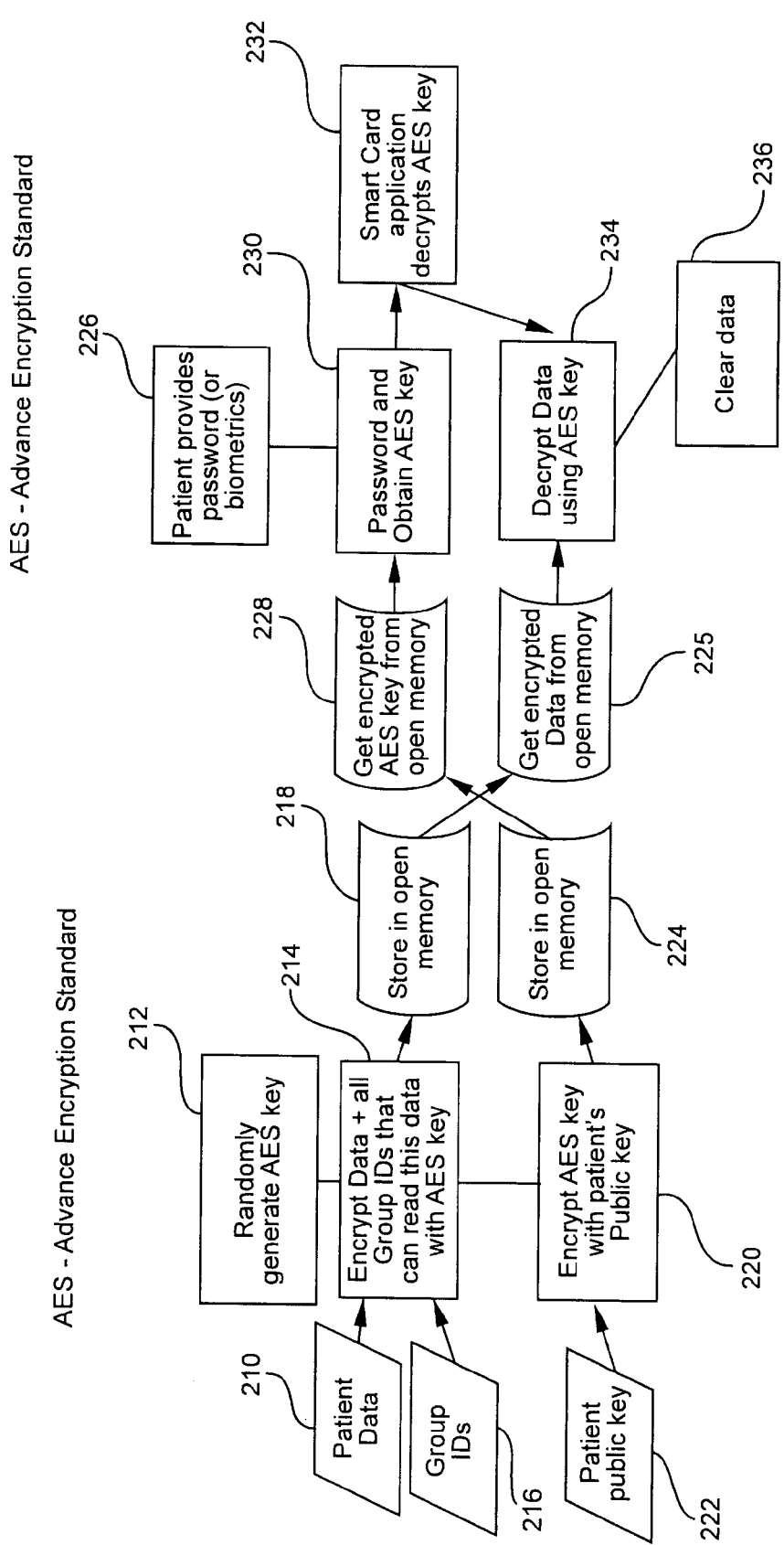
FIG. 12 is a flow diagram of an embodiment of a method of encrypting and decrypting data records according to the present invention.
Figure 13:
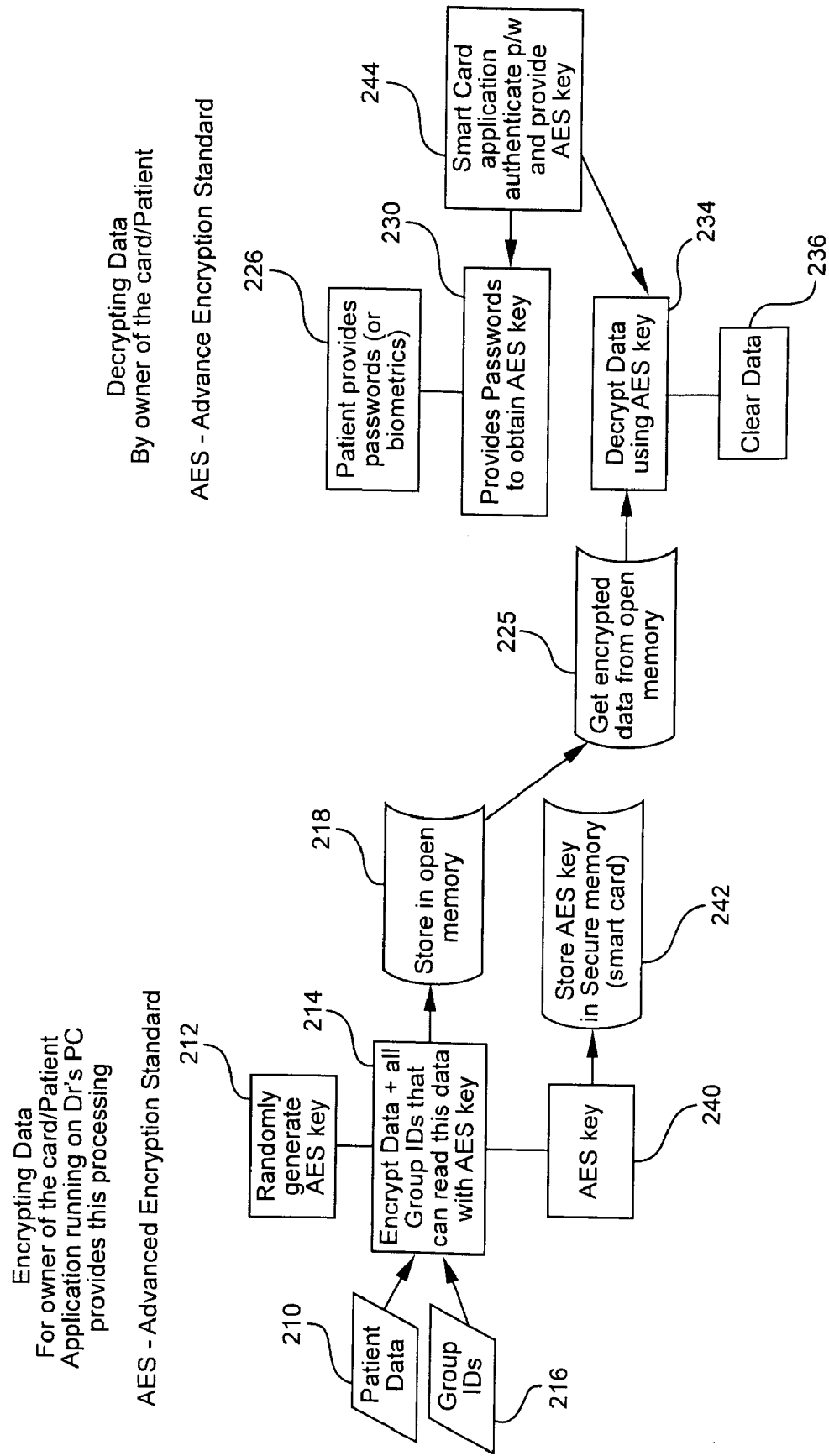
FIG. 13 is a flow diagram of another embodiment of a method of encrypting and decrypting data records according to the present invention.

Referring to FIG. 13, a method of encryption is provided similar to that shown in FIG. 12, except that the randomly-generated AES key is stored 242 in the secure memory (smart card). The AES key is only made available when the patient or the owner of the card provides a password or biometric input, or other identifier.

Preferably, the application runs on the host PC, and randomly generates 212 an AES (Advance Encryption Standard) key. The application then encrypts 214 patient data and all group ID access information, with the AES key. The encrypted data is then saved 218 in the open memory, and the AES key 240 is stored 242 in the secure memory/smart card.

Referring still to FIG. 13, a method of decrypting the data records is also similar to the example shown in FIG. 12, with the difference that the AES key can be obtained from the secure memory/smart card by the patient providing the password, biometrics, or other ID. Specifically, the patient provides the ID 226 to allow the decryption process. The password is sent to the smart card (secure memory engine) and the smart card verifies 230 the password or biometrics input. The AES key is then sent to the application after authenticating the password 244. The open AES key is used to decrypt 234 the patient data obtained from the open memory. The decrypted data is then available to be read by those whose Group ID is allowed 236.

Figure 14A:
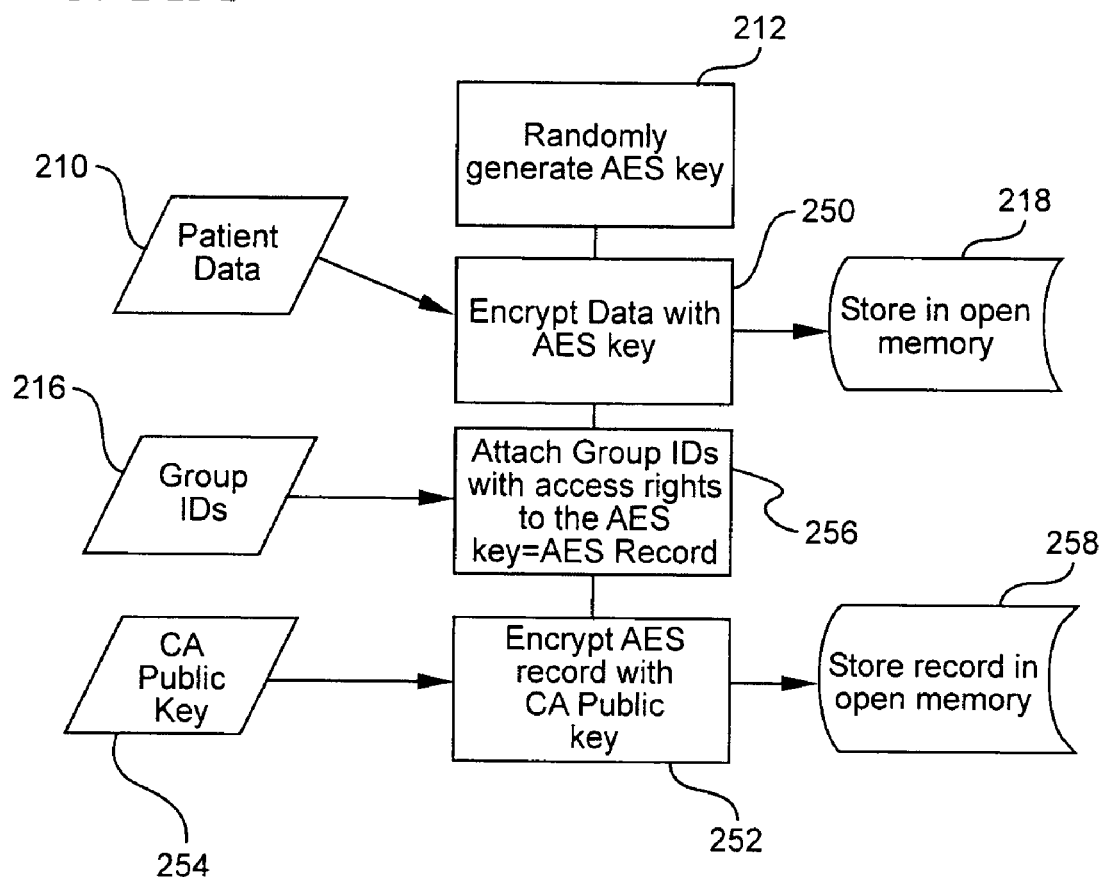
FIG. 14A is a flow diagram of an embodiment of a method of encrypting data records according to the present invention.

In another example shown in FIG. 14A, the patient data 210 and group ID's obtained from the cascading or group certificates are encrypted 250 using the randomly-generated AES key 212, while the Group IDs 216 associated with this data are encrypted 252 together with the AES key with an application specific Public key 254, which is provided, e.g., by the Card Administrator (CA). Again, it is assumed the application runs on a doctor's host PC. The application randomly generates an AES (Advance Encryption Standard) key 212, and then encrypts patient data with the AES key 250. The encrypted data is then saved in the open memory 218. All group IDs 216 allowed to read this data are appended to the AES key, and form the AES Record 256. The AES Record is encrypted 252 using the CA's Public key 254 and the AES Record is stored in open memory 258.

Figure 14B:
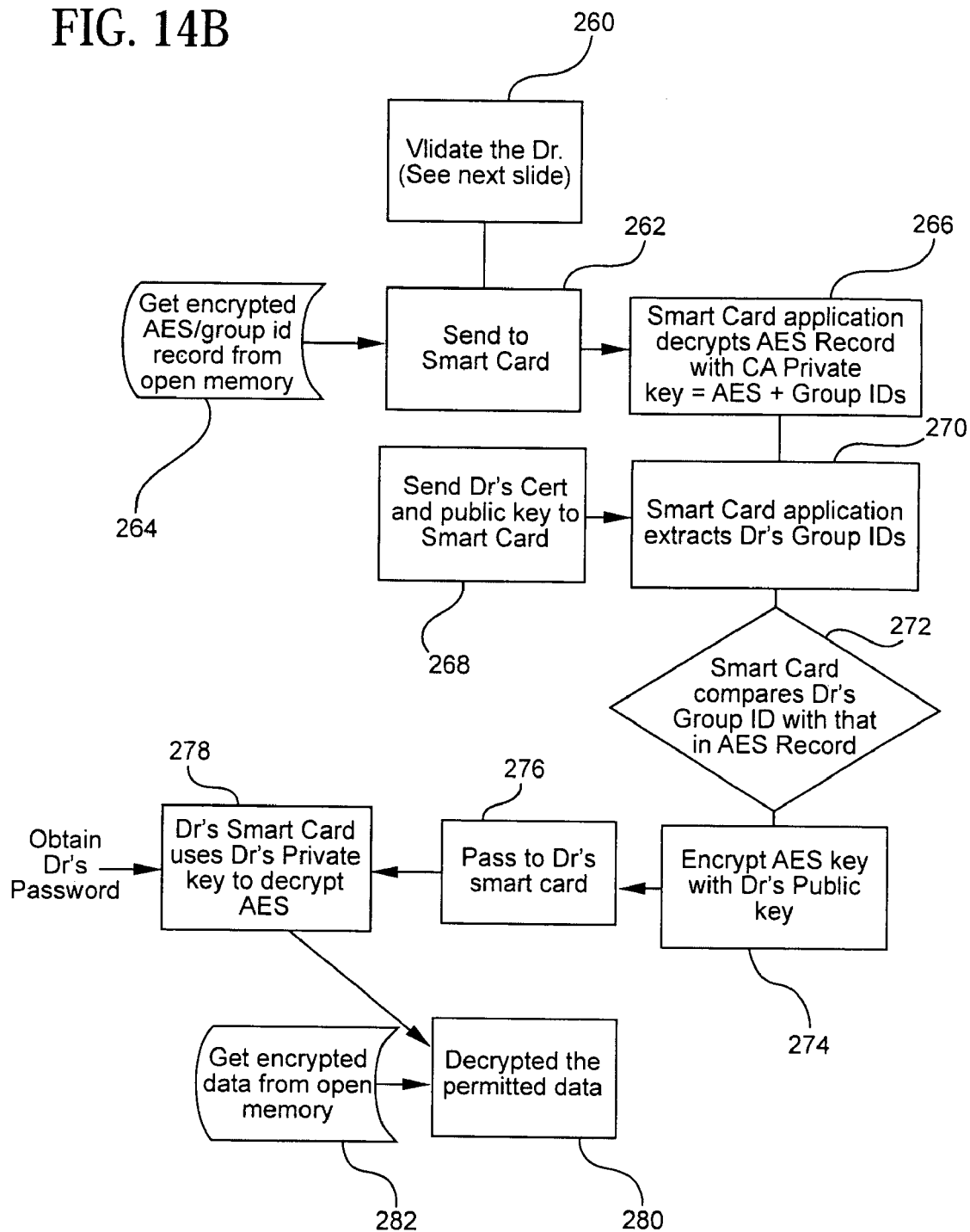
FIG. 14B is a flow diagram of an embodiment of a method of decrypting data records according to the present invention.

An example of decryption of the group ID's and data is shown in FIG. 14B, an entity is validated to make sure it has a valid ID. The system then checks to see whether that entity has access rights to the data. The system consists of the application running on the doctor's PC, the patient smart card, and the Doctor's card/smart card.

First, the doctor is validated (see FIG. 9) 260. The patient smart card receives 262 the encrypted AES Record 264. The patient smart card decrypts AES Record using an Application Specific or Card Administrator's (CA) Private key 266 to retrieve the AES key and the Group IDs. The patient smart card receives the Doctor's certificate and Doctor's Public key 268, and the patient smart card extracts the Doctor's Group ID 270. The Doctor's Group ID is then compared with the Group IDs that the patient smart card has extracted from the AES Record 272. If the Group IDs match, the AES key is encrypted with Doctor's public key 274. The encrypted AES key is passed to the Doctor's smart card 276, which decrypts the AES using Doctor's Private key 278. The AES is then used by the application to decrypt 280 the permitted data received 282 from the open memory.

Though the examples above have been provided for the example of a secure portable database for storing, managing, and accessing patient medical history in a secure multi-user environment, it is understood to those skilled in the art that the system and method of the present invention may be extended to many other uses, such as for sale or rental of music or videos downloaded onto a flash smart card.

Therefore, as a result of the present invention, a multi-user secure portable database and a system and method for providing and managing said database are provided.

Although the preferred embodiments of the present invention have been described with reference to the accompanying drawings, it is to be understood that the invention is not limited to those precise embodiments, and that other changes and modifications may be made by one skilled in the art without departing from the scope and spirit of the invention.

What is claimed is:

1. A method of providing, managing, and accessing a multi-user portable secure database comprising:
    providing a first portable database stored on a portable storage device with a secure portion and a non-secure portion;
    storing security components for encrypting and decrypting data files in the secure portion of the first portable database;
    storing encrypted data files in the non-secure portion of the first portable database; and
    controlling access to the encrypted data files using a first computer process being executed by a processing device, wherein said controlling access further comprises:
    assigning an access control matrix to each encrypted data file in the first portable database according to a hierarchical structure, wherein the access control matrix defines access rights of each user to each encrypted data file, the access control matrix assigning a level of access to each type of access;
    associating a user requesting access with one of the security components comprising a key for allowing the requested access to the first portable database in response to authentication of a second portable database against the first portable database by the first computer process, the second portable database comprising a secure portion; and
    allowing the requested access to one or more of the encrypted data files in the first portable database based on the authentication performed by the first computer process and in accordance with the access control matrix in the first portable database.

2. The method of claim 1, further comprising:
    issuing each user a certificate that identifies the issued user in the hierarchical structure; and
    additionally storing a private key associated with the certificate in the secure portion, wherein said allowing the requested access includes identifying the certificate with the user requesting access.

3. The method of claim 1, wherein the secure portion and the non-secure portion reside on at least one secure memory card or on at least one secure token comprising a processor.

4. The method of claim 1, the method further comprising accessing the secure portable database, said accessing comprising authenticating the user requesting access, said authenticating comprising providing authenticating data to identify the user requesting access.

5. The method of claim 4, wherein the authenticating data comprises at least one of biometric data and keypad input.

6. The method of claim 5, wherein the biometric data comprises a fingerprint.

7. The method of claim 5, wherein the keypad input comprises one of a personal identification number and a password.

8. The method of claim 4, wherein said authenticating further comprises comparing the authenticating data to a known identifier of the user requesting access, wherein the known identifier is stored in the secure portion.

9. The method of claim 4, wherein the stored security components include a private key and a certificate of the user requesting access, wherein the certificate comprises a public key of the user and identifies the user in the hierarchical structure, and wherein said accessing further comprises:
    retrieving the private key and the certificate of the user requesting access from the secure portion in response to said authenticating.

10. The method of claim 9, wherein a type of access requested is selected from a group comprising Create, Read, Update and Delete, and further wherein the level of access assigned to each type of access is selected from a group comprising Restricted, Allowed, Grant and Supergrant.

11. The method of claim 10, wherein the type of access requested is the Create type of access, the user requesting access writing a new file to the portable secure database, said writing comprising:
    retrieving the certificate in response to said authenticating;
    automatically embedding the hierarchical structure obtained from the certificate in the new file;
    automatically generating and embedding the access control matrix;
    automatically encrypting the new file according to the access control matrix; and
    storing the encrypted new file in the non-secure portion.

12. The method of claim 11, said writing further comprising digitally signing the encrypted new file.

13. The method of claim 11, wherein the hierarchical structure comprises levels identifying each user, groups to which each user belongs, and a world that includes all groups in the portable secure database, and wherein
said automatically encrypting comprises:
identifying every user and group to which the level of access for at least one type of access to the new file is not Restricted according to the access control matrix;
retrieving a public key for every identified users and groups; and
encrypting the new file with the public keys for the identified users and groups.

14. The method of claim 11, said writing further comprising:
providing a log comprising a hash of each encrypted data file to verify integrity of the portable secure database;
creating a hash of the encrypted new file;
updating the log in response to said writing the encrypted new file; and
digitally signing the log with a card administrator key.

15. The method of claim 11, said writing further comprising:
time stamping the encrypted new file.

16. The method of claim 11, the method further comprising exporting the encrypted data files to at least one of a local or remote backup storage space.

17. The method of claim 10, wherein the requested type of access is the Read type of access, the user requesting access to read one of the encrypted data files, said reading comprising:
retrieving the one of the encrypted data files from the non-secure portion, the one of the encrypted data files being encrypted with the public key of the user requesting access;
retrieving the private key from the secure portion upon authentication;
decrypting the one of the encrypted data files with the private key in accordance with the level of access provided in the access control matrix.

18. The method of claim 17, wherein the one of the encrypted data files is digitally signed, the method further comprising:
accessing a digital signature attached to the one of the encrypted data files;
obtaining a certificate of a user owning the digital signature, the certificate comprising the owner's public key; and
validating the digital signature using the owner's public key.

19. The method of claim 4, said authenticating further comprising:
providing challenge data in response to said retrieving;
providing response data by digitally signing the challenge data with the private key;
retrieving the public key from a certificate; and
using the public key to validate the response data.

20. The method of claim 19, said authenticating further comprising validating an expiration date of the certificate, wherein the expiration date is stored in the certificate, said validating comprising comparing the expiration date to a trusted time stamp.

21. The method of claim 1, further comprising:
providing a counter associated with one of the encrypted data files; and
stepping the counter in response to the one of the encrypted data files being successfully updated.

22. The method of claim 1, wherein the portable secure database is a medical database comprising a plurality of personalized data cards, wherein a type of access requested is selected from a group comprising Create, Read, Update and Delete, further wherein the level of access assigned to each type of access is selected from a group comprising Restricted, Allowed, Grant and Supergrant, and wherein the method further comprises:
initializing each data card with identifying records, wherein said initializing is performed by a card administrator; and
issuing a certificate and a private key associated with an owner of each of the plurality of data cards on the owner's card.

23. The method of claim 22, wherein one of the encrypted files is a pharmaceutical prescription with a number of refills, the method further comprising providing a counter associated with the number of refills; and
decrementing the counter in response to a pharmacist filling the pharmaceutical prescription.

24. The method of claim 22, wherein the hierarchical structure comprises levels identifying each user, groups to which each user belongs, and a world that includes all groups in the portable secure database,
wherein the groups include an emergency medical team group, a hospital group, a physician group, a patient group, and a health insurance company group, and
wherein at least one of the users is a patient in the patient group, one of the plurality of data cards being a patient card owned by the patient, the patient card comprising the patient's encrypted personal medical records;
the method further comprising:
allowing access to any user included in the world of users of the medical database to read encrypted data files comprising identifying data from the patient card, said allowing comprising assigning the Allowed level of access to the Read type of access to the world level in the access control matrix assigned to the identifying encrypted data files.

25. The method of claim 24, wherein the identifying data comprises at least one of a name, a card identification number, a date of birth, an address, a social security number, a photograph, a religious preference, an image of a driver's license, organ donor information, and special medical conditions.

26. The method of claim 25, wherein the user requesting access is a member of the emergency medical team group, the method further comprising allowing access to the emergency medical team user to read encrypted data files comprising emergency records and to write new encrypted emergency records comprising an access matrix including the Allowed level of access to the Read type of access to the emergency medical team group and to the hospital group.

27. The method of claim 26, wherein the emergency records comprise at least one of blood type, allergies, epilepsy, diabetes, heart conditions, metal plates, pace makers, and other special medical conditions, and
wherein the new emergency records comprise vital signs, blood pressure, and other medical data collected during emergency treatment.

28. The method of claim 24, the method further comprising the patient assigning to one of the encrypted personal medical records a level of access selected from Allowed, Grant, or Supergrant to a Read type of access to one of the physicians in the physician group.

29. The method of claim 28, the patient assigning further comprising:
authenticating the patient; and authenticating the one of the physician with the patient card present, wherein the one of the physicians acquires the selected level of access in response to said authenticating acts.

30. The method of claim 24, wherein a type of access requested is the Create type of access, further wherein the user requesting the Create type of access is one of the physicians, the one of the physicians requesting access to write a medical record to the patient card, said writing comprising:
   authenticating the one of the physician;
   embedding the hierarchical structure;
   embedding the access control matrix;
   providing a randomly generated key;
   encrypting the medical record with the randomly generated key;
   encrypting each certificate corresponding to each group to which a level of access other than Restricted has been assigned according to the access control matrix with the randomly generated key;
   attaching the encrypted certificates to the encrypted medical record; and
   storing the encrypted medical record to the non-secure portion of the patient card.

31. The method of claim 30, said writing further comprising:
   encrypting the randomly generated key with the patient public key; and
   storing the encrypted randomly generated key on the non-secure portion of the portable database.

32. The method of claim 31, wherein a type of access requested is the Read type of access to the encrypted medical record on the patient card, said reading comprising:
   authenticating the user requesting read access;
   authenticating the patient;
   retrieving the patient private key and the encrypted randomly generated key in response to said authenticating;
   decrypting the encrypted randomly generated key automatically with the patient private key;
   decrypting the medical record with the randomly generated key; and
   allowing access to the user requesting read access in accordance with the access control matrix.

33. The method of claim 30, wherein said writing further comprises storing the randomly generated key on the secure portion of the patient data card, further wherein a type of access requested is the Read type of access to the encrypted medical record on the patient card, said reading comprising:
   authenticating the patient;
   authenticating a user requesting read access;
   retrieving the patient private key and the randomly generated key in response to said authenticating;
   decrypting the medical record with the randomly generated key; and
   allowing access to the user requesting read access in accordance with the access control matrix.

34. The method of claim 30, said writing further comprising:
   providing a Card Administrator public key; and
   additionally encrypting the randomly generated key and the attached certificates with the Card Administrator public key.

35. The method of claim 34, wherein a type of access requested is the Read type of access to the encrypted medical record on the patient card, said reading comprising:
   providing a Card Administrator private key; and
   decrypting the randomly generated key and the attached certificates with the Card Administrator private key.

36. The method of claim 1, wherein the first portable database comprises a portable database card associated with a first holder and the second portable database comprises a portable database card associated with a second holder.

37. The method of claim 36, wherein the first holder is a patient and the second holder is at least one of a doctor, health care provider, pharmacist, medical insurance company, and an Emergency Medical team (EMI) worker.

38. A multi-user system for storing, updating, and accessing secure data records, said system comprising:
   a first portable database device comprising:
      a secure portion and a non-secure portion;
      a data structuring module configured to embed a hierarchical structure for each user into each secure data record in the first portable database device, wherein the hierarchical structure identifies each user and allows for assigning access rights to each secure data record; and
      an access control module configured to embed a security element into each secure data record and to cooperate with a security management module for managing a plurality of security elements associated with a plurality of users and with said data structuring module,
      wherein said access control module is configured to assign the access rights for each user to each secure data record and to allow a user access to a secure data record in accordance with the assigned access rights, and
      wherein the non-secure portion of the first portable database comprises the secure data records and the secure portion comprises at least one of the plurality of security elements; and
   a second portable database device comprising a secure portion and configured to hold authentication information, wherein the second portable database device is authenticated against the first portable database device using the authentication information before the user is permitted to access the first portable database device.

39. The system of claim 38, further comprising a management module comprising:
   a user authentication module to identify and authenticate a user requesting access; and
   a key management module configured to manage and store the plurality of security elements for embedding into the secure data records in cooperation with said access control module.

40. The system of claim 39, wherein the user authentication module is configured to accept at least one of biometric data and keyboard input.

41. The system of claim 38, wherein the plurality of security elements include encryption keys and certificates associated with the plurality of users.

42. The system of claim 38, wherein the hierarchical structure includes levels identifying each user, groups to which each user belongs, and a world that includes all groups in the first portable database device.

43. The system of claim 42, wherein the access rights comprise a level of access assignable to each type of access for each user according to the hierarchical structure.

44. The system of claim 43, wherein the assignable levels of access include Restricted, Allowed, Grant and Supergrant.

45. The system of claim 44, wherein the types of access include Create, Read, Update, And Delete.

46. The system of claim 45, wherein the secure data records comprise patient medical records and wherein the first portable database device comprises a plurality of data cards, wherein the groups include an emergency medical team group, a hospital group, a physician group, a patient group, and a health insurance company group, and
wherein at least one of the users is a patient in the patient group, at least one of the plurality of data cards being a patient card owned by a patient from the patient group, the patient card comprising the patient's encrypted personal medical records.

47. The system of claim 38, wherein the secure data files comprise at least one of textual data, digital images, digital audio data, and digital video data.

48. A multi-user system adapted to store, update, and access secure data records using, said system comprising:
a portable database device, said portable database device comprising:
a secure portion and a non-secure portion;
a first data path adapted to provide access to the security element in the secure portion and a second data path adapted to provide access to the secure data record in the non-secure portion;
a data structuring module, configured to embed a hierarchical structure for a user into a secure data record in the portable database device, wherein the hierarchical structure identifies the user and allows for assigning access rights to the secure data record; and
an access control module, configured to embed a security element into the secure data record and to cooperate with a security management module for managing a security element associated with a user and said data structuring module,
wherein said access control module is configured to assign the access rights for the user to the secure data record and to allow a user access to the secure data record in accordance with the assigned access rights, and
wherein the non-secure portion of the portable database device comprises the secure data records and the secure portion comprises at least one of the plurality of security elements.

49. A method of providing, managing, and accessing a multi-user portable secure database comprising:
providing a portable database stored on a portable storage device with a secure portion and a non-secure portion;
storing security components adapted to encrypt and decrypt data files in the secure portion of the portable database;
storing encrypted data files in the non-secure portion of the portable database;
storing, in the portable database, an audit log associated with at least one of the encrypted data files in the portable database, the audit log providing information concerning modifications to the at least one of the encryption data files;
hashing the audit log using a first computer process being executable by a processing device; and
controlling access to the encrypted data files using a second computer process being executable by the processing device, wherein said controlling access step further comprises:
assigning an access control matrix to each encrypted data file in the portable database according to a hierarchical structure, wherein the access control matrix defines access rights of each user to each encrypted data file, the access control matrix assigning a level of access to each type of access;
associating a user requesting access with one of the security components comprising a key for allowing the requested access to the portable database; and
allowing the requested access to one or more of the encrypted data files in the portable database using the second computer process in accordance with the access control matrix in the portable database.

50. The method of claim 49, further comprising rehashing the audit log, thereby ensuring that the at least one of the encrypted data files has not been tampered with.

* * * * *